(12) United States Patent
Guimond et al.

(10) Patent No.: US 6,514,219 B1
(45) Date of Patent: Feb. 4, 2003

(54) SYSTEM AND METHOD FOR AUTOMATED BIOMECHANICAL ANALYSIS AND THE DETECTION AND CORRECTION OF POSTURAL DEVIATIONS

(75) Inventors: Sylvain Guimond, Ste-Anne-de-Sorel (CA); David H. McFarland, Mount Royal (CA); Alfonso Lombardi, St-Lambert (CA); Martin C. Normand, Cap-de-la-Madeleine (CA)

(73) Assignee: Biotonix Inc., Montréal (CA)

( * ) Notice: Subject to any disclaimer, the term of this patent is extended or adjusted under 35 U.S.C. 154(b) by 99 days.

(21) Appl. No.: 09/714,830

(22) Filed: Nov. 17, 2000

(51) Int. Cl.⁷ .......................... A61B 5/103; A61B 5/117
(52) U.S. Cl. ........................................ 600/595; 600/587
(58) Field of Search .................. 600/300, 301, 600/587, 594, 595, 414, 426; 128/898, 920, 923; 705/2, 3

(56) References Cited

U.S. PATENT DOCUMENTS

| | | | |
|---|---|---|---|
| 4,786,925 A | * 11/1988 | Landwehr | 353/28 |
| 4,813,436 A | 3/1989 | Au | |
| 4,971,069 A | 11/1990 | Gracovetsky | |
| 5,072,294 A | * 12/1991 | Engle | 348/172 |
| 5,080,109 A | * 1/1992 | Arme, Jr. | 33/515 |
| 5,203,346 A | 4/1993 | Fuhr et al. | |
| 5,482,048 A | * 1/1996 | Johnson | 382/128 |
| 5,544,649 A | 8/1996 | David et al. | |
| 5,630,422 A | 5/1997 | Zanakis | |
| 5,679,004 A | 10/1997 | McGowan et al. | |
| 5,754,121 A | 5/1998 | Ward et al. | |
| 5,791,342 A | 8/1998 | Woodard | |
| 5,800,364 A | 9/1998 | Glennie et al. | |
| 5,810,747 A | 9/1998 | Brudny et al. | |
| 5,823,958 A | 10/1998 | Truppe | |
| 5,890,906 A | 4/1999 | Macri et al. | |
| 5,891,060 A | 4/1999 | McGregor et al. | |
| 5,904,484 A | 5/1999 | Burns | |
| 5,954,674 A | 9/1999 | Fuhr | |
| 5,991,701 A | 11/1999 | Triano | |
| 6,007,459 A | 12/1999 | Burgess | |
| 6,039,688 A | 3/2000 | Douglas et al. | |
| 6,047,259 A | 4/2000 | Campbell et al. | |
| 6,056,671 A | 5/2000 | Marmer | |
| 6,280,395 B1 | * 8/2001 | Appel et al. | 600/546 |
| 6,383,148 B1 | * 5/2002 | Pusch et al. | 128/898 |

* cited by examiner

Primary Examiner—Max F. Hindenburg
Assistant Examiner—Charles Marmor, II
(74) Attorney, Agent, or Firm—James Anglehart; Ogilvy Renault

(57) ABSTRACT

The present invention relates to a method of acquiring biomechanical position data for use in postural analysis, where a plurality of scanable markers are attached on the patient at marker positions, the patient is instructed to stand in normal posture, and the markers attached to the patient are scanned to obtain position data for each of them. The present invention also relates to a method for calculating postural deviation values in a patient where an angle of deviation value and distance of deviation value with respect to the plumb line position value are calculated using the biomechanical position data. The present invention further relates to a method of providing posture health care using a distributed system.

35 Claims, 16 Drawing Sheets

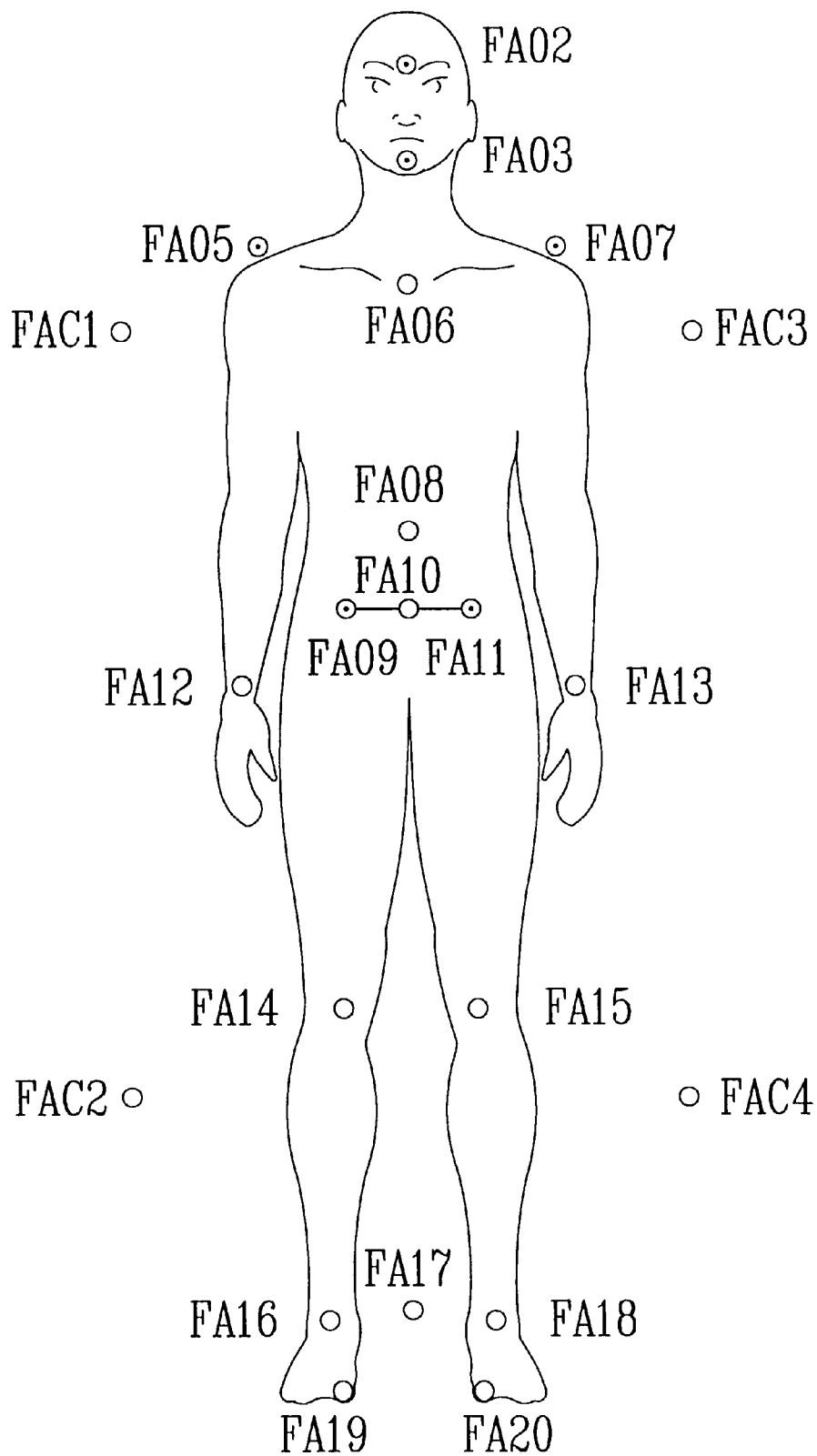
FIG_1

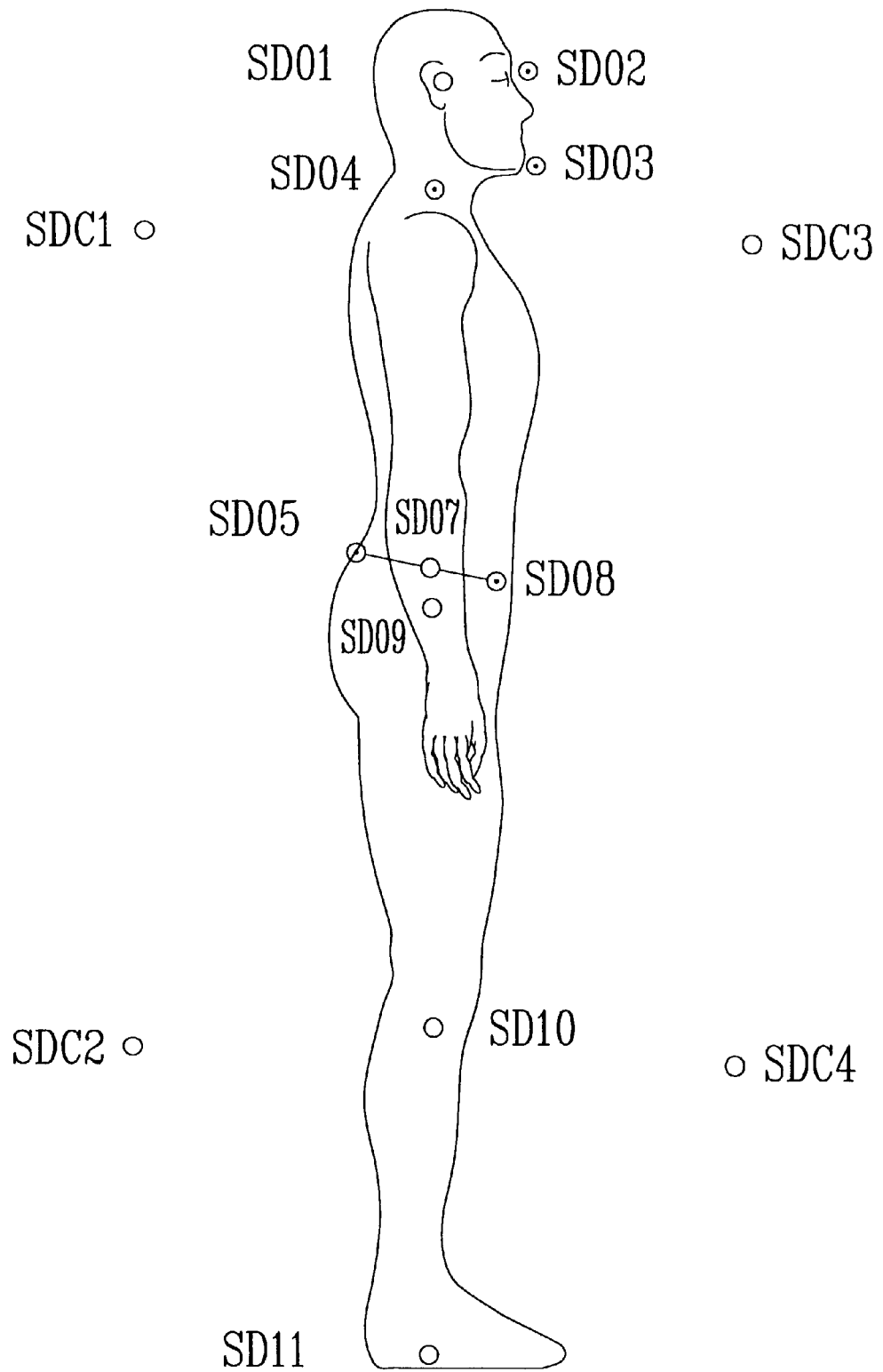
FIG_2A

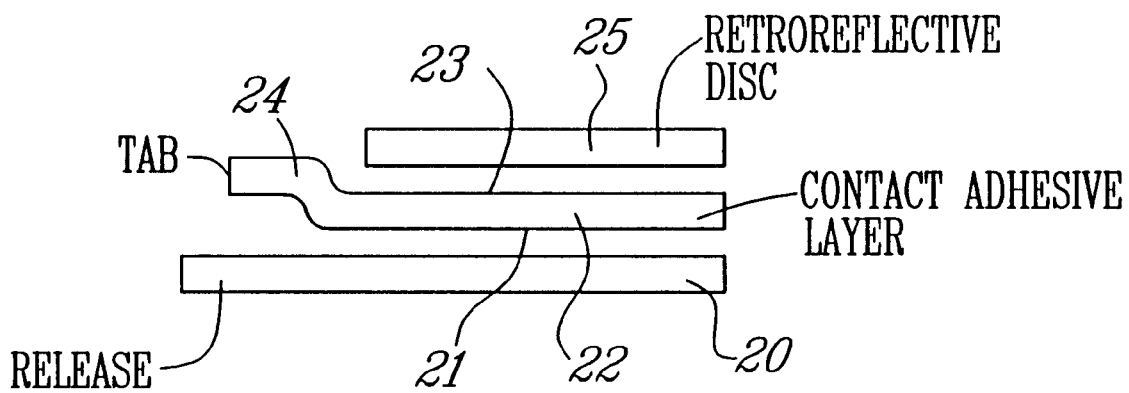
FIG_4
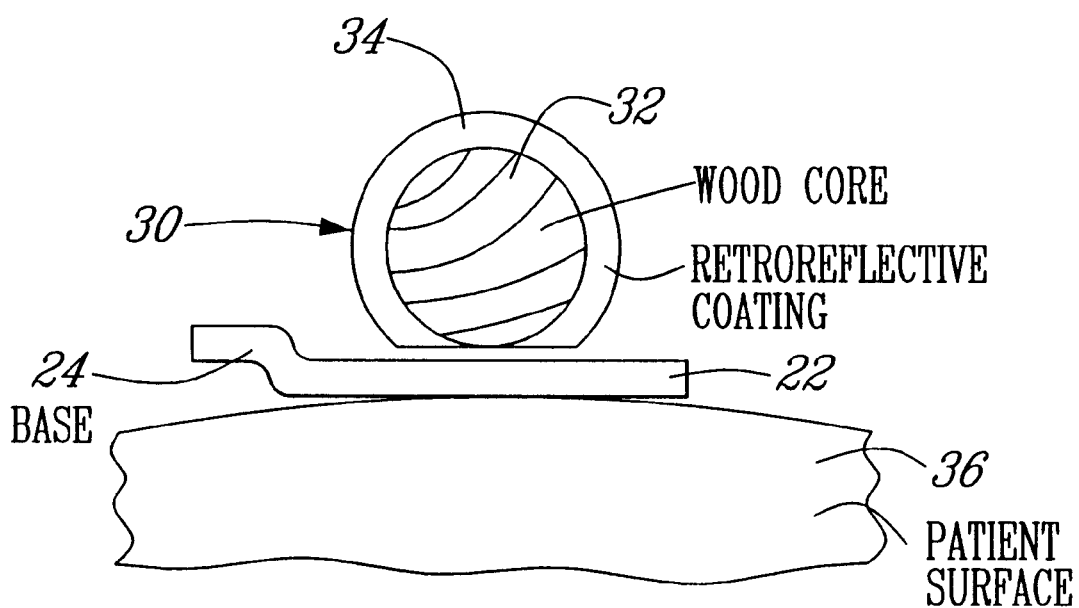
FIG_5

FIG_7

FIG_9

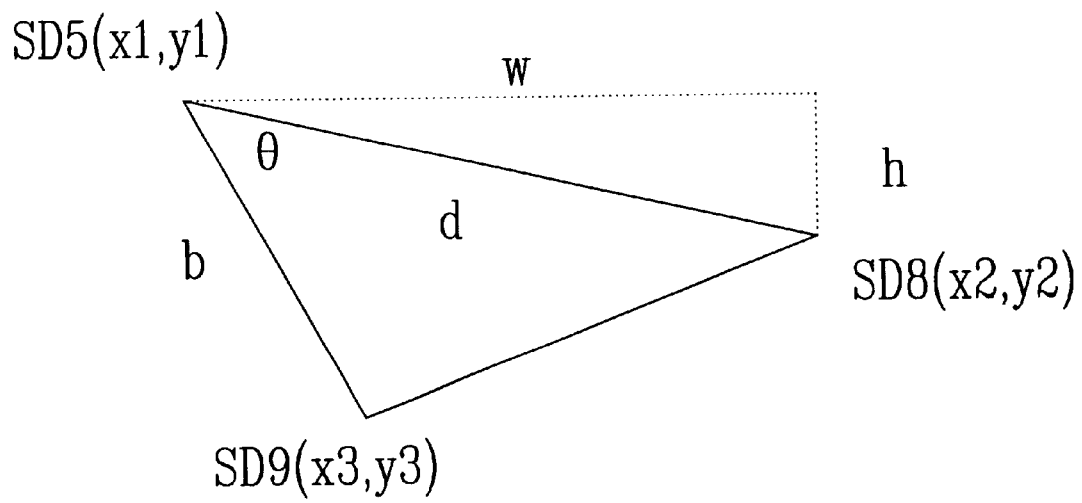
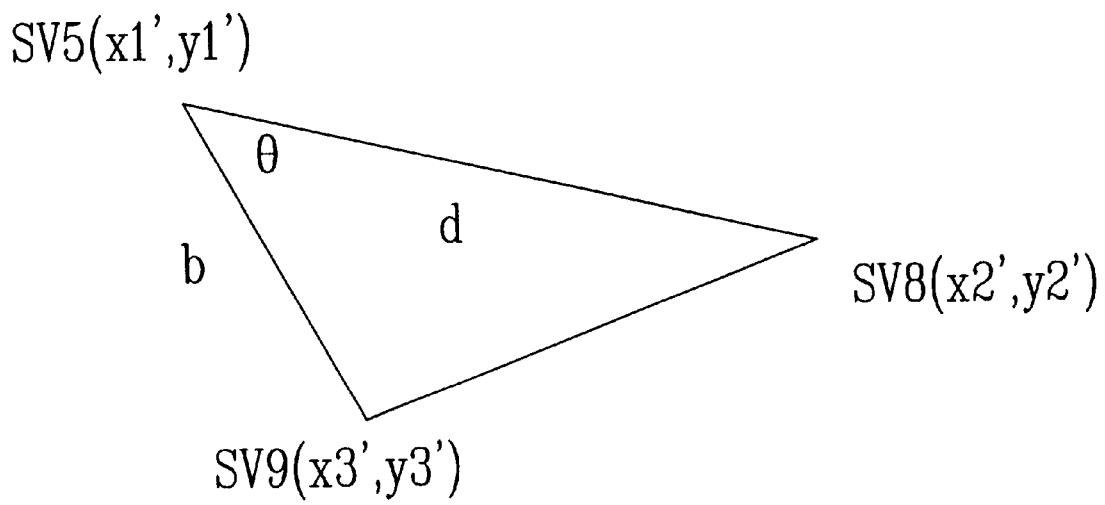
FIG_12

Identification
- User ID : jf1708200002
- Name: Posterior Head Translation
- Birthdate : Thursday, January 01, 1970
- Sex: Male
- Height : 67.0 in
- Weight: 170.0 lbs
- Activity Level: Inactive Evaluator : Jean-Francois Normandin Lateral View Deviations from Vertical Alignment

| Segment | Direction | Angle |
|---|---|---|
| Head to Shoulders | Posterior | 8.5° |
| Shoulders to Pelvis | Anterior | 3.8° |
| Pelvis to Hips | Posterior | 13.0° |
| Hips to Knees | Posterior | 1.5° |
| Knees to Feet | Anterior | 2.9° |

Note: The ideal angle should be 0°.

Distances from the Vertical Axis

| Reference Point on | Direction | Distance |
|---|---|---|
| Head | | 0.0 in |
| Shoulders | Anterior | 0.7 in |
| Pelvis | Posterior | 0.4 in |
| Hips | Anterior | 0.4 in |
| Knees | Anterior | 0.8 in |

Note: The ideal distance should be 0 in.

Moments of Force and Reaction Forces

| Segment | Actual weight | Lever arm | Moment of force | Joint reaction force | Effective weight |
|---|---|---|---|---|---|
| Head | 14.3 lbs | 0.7 in | -1.2 Nm ↶ | 92.8 N | 20.9 lbs |
| Head and Trunk | 113.6 lbs | 0.4 in | 5.3 Nm ↷ | 611.5 N | 137.6 lbs |

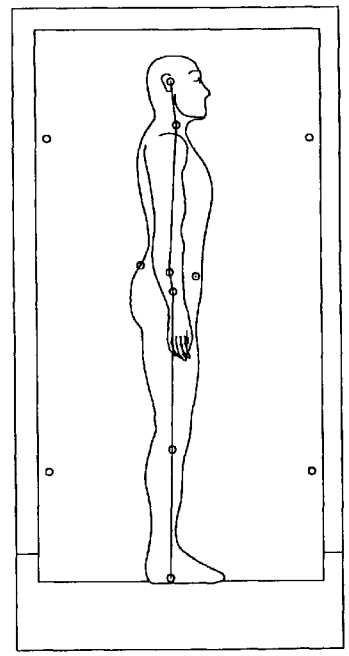

FIG. 13

Postural Deviations and Associated Exercises and Stretching

| Postural Deviation | # | Movement | Action | Recommended by |
|---|---|---|---|---|
| Posterior pelvic tilt | 1 | Hip Extension (left) | Stretch | System |
| | 2 | Hip Extension (right) | Stretch | System |
| | 3 | Hip Flexion (left) | Contract | System |
| | 4 | Hip Flexion (right) | Contract | System |
| | 5 | Trunk flexion | Stretch | System |
| | 6 | Trunk lumbar extension | Contract | System |
| Translation of the head (right) | 7 | Neck head lateral flexion (left) | Contract | System |
| | 8 | Neck head lateral flexion (right) | Stretch | System |
| Extension of the head | 9 | Neck head extension | Stretch | System |
| | 10 | Neck head flexion | Contract | System |
| | 11 | Scapula Adduction | Stretch | System |

FIG_14

Exercise and Stretching Schedule

| Period | # | Name | Movement | Repetitions |
|---|---|---|---|---|
| Week 1-2 | 1 | Hamstring stretch | 1 | 3X 30 Sec. |
| | 4 | Hamstring stretch | 2 | 3X 30 Sec. |
| | 7 | Squat | 3,4 | 3x 10-15 Reps |
| | 9 | Cobra | 5 | 3X 30 Sec. |
| | 10 | Prone lumbar extension with hands on the lower back | 6 | 3x 10-15 Reps |
| | 12 | Cervical strengthening | 7 | 10X 6 Sec. |
| | 14 | Left lateral flexion | 8 | 3X 30 Sec. |
| | 17 | Forward neck flexion | 9 | 3X 30 Sec. |
| | 18 | Cervical strengthening | 10 | 10X 6 Sec. |
| | 19 | Scapula adductor stretch with your hands behind your back | 11 | 3X 30 Sec. |
| Week 3-6 | 2 | Hamstring stretch | 1 | 3X 30 Sec. |
| | 5 | Hamstring stretch | 2 | 3X 30 Sec. |
| | 8 | Unilateral squat | 3,4 | 3x 10-15 Reps |
| | 9 | Cobra | 5 | 3X 30 Sec. |
| | 11 | Seated lumbar extension | 6 | 3x 10-15 Reps |
| | 13 | Supine cervical strengthening | 7 | 10X 6 Sec. |
| | 15 | Supine lateral flexion to the left | 8 | 3X 30 Sec. |
| | 17 | Forward neck flexion | 9 | 3X 30 Sec. |
| | 18 | Cervical strengthening | 10 | 10X 6 Sec. |
| | 20 | Scapula adductor stretch with your arms crossed | 11 | 3X 30 Sec. |
| Week 7-10 | 3 | Hamstring stretch | 1 | 3X 30 Sec. |
| | 6 | Hamstring stretch | 2 | 3X 30 Sec. |
| | 8 | Unilateral squat | 3,4 | 3x 10-15 Reps |
| | 9 | Cobra | 5 | 3X 30 Sec. |
| | 11 | Seated lumbar extension | 6 | 3x 10-15 Reps |
| | 13 | Supine cervical strengthening | 7 | 10X 6 Sec. |
| | 16 | Left lateral flexion with rotation to the right | 8 | 3X 30 Sec. |
| | 17 | Forward neck flexion | 9 | 3X 30 Sec. |
| | 18 | Cervical strengthening | 10 | 10X 6 Sec. |
| | 20 | Scapula adductor stretch with your arms crossed | 11 | 3X 30 Sec. |

FIG. 15

Exercises and Stretching

1 - Hamstring stretch

Position
1. Place the heel of the foot of the working leg on a chair or something of equivalent height so that the leg is flexed at the hip and extended at the knee.
2. Gently flex the supporting leg at the hip and knee. Place one hand on the supporting leg's thigh and the other hand on the outer part of the working leg's thigh.

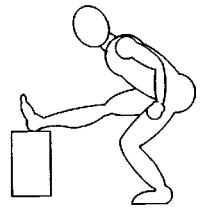

Action
Flex the supporting leg at the knee until you feel a pulling sensation in the working leg. Hold the stretch for the specified time, gradually relax and repeat as indicated.

Specific Objective
Improve hamstring muscle group flexibility (hip extensors, knee flexors).
Contraction type:
Static stretch 2 - Hamstring stretch Position
1. Lie on your back with one leg flexed at the hip and knee, foot flat on the floor.
2. Flex the working leg at the hip and knee, and gently pull it in to the chest with your hands placed behind the knee.

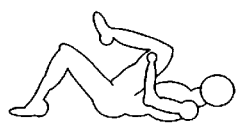

Action
Pull the knee of the working leg in towards the chest, keeping the leg flexed at the knee. When you feel a pulling sensation in the back of the thigh, hold the stretch for the specified time, gradually relax and repeat as indicated.

Specific Objective
Improve hamstring muscle group flexibility (hip extensors).
Contraction type:
Static stretch

FIG. 16

SYSTEM AND METHOD FOR AUTOMATED BIOMECHANICAL ANALYSIS AND THE DETECTION AND CORRECTION OF POSTURAL DEVIATIONS

The present invention relates to a system and method for the biomechanically accurate measurement of posture and for providing a patient with a suitable corrective exercise program. More particularly, the present invention relates to a system and method to automatically analyse the location of anatomical markers placed over skeletal landmarks to obtain biomechanical parameters; a system and method that uses these biomechanical data to automatically detect and/or quantify postural deviations from correct anatomical alignment; a system and method to automatically generate corrective exercise routines. The present invention also relates to the use of the Internet to provide a distributed system for patient care involving image acquisition in a clinical environment, data analysis at a central server and communication between the central server and the health-care professional as well as potential follow-up and feedback between the patient and either the health-care professional or the central server or both.

BACKGROUND OF THE INVENTION

Description of Prior Art

A tree trunk grows straight up and tree branches are symmetrical around this solid core to provide a "posture" to withstand the effects of wind and gravity. We too have an optimal posture that allows us to function most efficiently. As builders and architects use plum lines to arrange the walls and supporting structures of a home, we use plumb lines to define this ideal postural alignment. In correct posture, a plumb line dropped from you ear will go through your shoulder, the middle of your pelvis, the middle of your knee, and the front of your anklebone. Your head, trunk, pelvis and knees are "stacked" one on top of the other. Deviations from this positioning can have negative consequences to your health and well being, and correcting postural alignment can make a person look and feel better. Ideal or optimal posture minimizes energy expenditure and muscle work necessary to maintain deviant posture in the face of gravitational forces. As patients become more and more proactive in their choice or health care, they will certainly demand amelioration of their disordered posture. For example, lower back pain has often been attributed to abnormal postural relationships between body segments, and is frequently a cause of patient complaints to family care physicians.

Typically, practitioners are content with a basic appreciation of a client's posture. Systematic biomechanical analyses are rarely performed because they are time intensive and require specialized equipment. Instead, only qualitative observations are often made. Specialists, such as Chiropractors and physiotherapists are sometimes trained to make postural assessments, often employing qualitative measures to assess posture and determine corrective measures. Practitioners may refer to these specialists, but again, the procedures are time and labor intensive and consequently, are expensive for the patient, who may or may not have insurance to cover these expenses. Further, qualified medical practitioners, such as family practice physicians, may want to perform such analyses but lack the specialized equipment or training to accurately assess posture based on observations alone. Consequently, a cost effective and highly automatic system is needed to assist practitioners in effective assessment and treatment of postural difficulties.

In 1998, Tonix Santé introduced a biomechanical computation system based on the manual identification of anatomical markers from analog video images. Clinicians manually identified the location of these markers on images and some biomechanical computations were performed. However, it took a long time to place markers because common scotch tape first had to be applied to patients and then markers affixed to this adhesive. There was also no automatic detection of marker placement, no automatic detection of postural deviations, and no automatic generation of exercise routines to ameliorate postural deviations. The placement of anatomical markers on the body's surface was not based on any established model of ideal postural alignment. In other automated processes for postural evaluation, the markers are placed on the patient's loose-fitting clothes, such a method lacks precision, because first, it is difficult to determine the location of appropriate structural landmarks through loose-fitting clothing, and the position of the markers may move because clothing can move in relationship to the skin surface. Also, markers can not be safely placed on the patient's skin because they are not compliant with hypoallergenic requirements.

Another deficiency of the actual method to evaluate and correct patient's posture is the loss of control of the health-care practitioner in the treatment given to his or her patient when he or she refers the patient to a specialist such as chiropractor or physiotherapist. The patient has to take several appointments from several potential specialists. Furthermore, no health-care practitioner or specialist alone can benefit from experience with thousands of patients and be able to correlate biomechanical information from these patients with appropriate treatment and results obtained. There is neither a way to share experience in an efficient way between several health-care practitioners and/or specialists treating this many patients. There is also no way to provide a quantified follow-up of progress.

SUMMARY OF THE INVENTION

One aim of the present invention is to provide a process and apparatus to acquire biomechanical position data in selecting marker positions referenced with respect to the patient's skeletal anatomy by one of skin surface features having minimal variability from one patient to the next and skeletal features palpable from a skin surface of the patient and in attaching a scanable marker on the patient at each of the marker positions, these marker positions being used to calculate the positions of body segments.

Another aim is to provide a method to analyze these body segment positions to obtain body segment biomechanical parameters and deviations.

An other aim of the present invention is to provide a method to use these biomechanical deviation values to determine postural deviations and corrective exercises to rectify these deviations.

Another aim of the present invention is to use the Internet to provide a distributed system for patient care involving image acquisition in a clinical environment, data analysis at a central server and communication between the central server and the health-care professional as well as potential follow-up and feedback between the patient and either the health-care professional or the central server or both.

In accordance with the present invention there is provided a method of acquiring biomechanical position data for use in postural analysis, this method comprising the steps of:

a) selecting a plurality of marker positions referenced with respect to an anatomy of a patient by one of:

skin surface features having minimal variability from one patient to the next; and skeletal features palpable from a skin surface of the patient;

b) attaching a scanable marker on the patient at each of the marker positions, the step of attaching including palpating the patient to define at least some of the marker positions; instructing the patient to stand relaxed and in normal posture; and c) scanning the markers on the patient to obtain position data for each of the marker positions.

The method in accordance with a preferred embodiment of the present invention, wherein the patient is scanned from a front, side and rear viewpoints.

The method in accordance with a preferred embodiment of the present invention, wherein the step of scanning comprises photographing the patient against a backdrop, the markers comprising contrasting visual markers, the backdrop including a plurality of scale and orientation reference marker points.

The method in accordance with a preferred embodiment of the present invention, wherein the markers comprise an adhesive layer for sticking to the patient.

The method in accordance with a preferred embodiment of the present invention, wherein the step of photographing comprises using a digital camera with a flash to obtain digital images, the markers comprising retroreflective markers.

The method in accordance with a preferred embodiment of the present invention, wherein some of the markers are scanned from more than one of the viewpoints and comprise retroreflective spheres.

The method in accordance with a preferred embodiment of the present invention, wherein the step of instructing the patient to stand relaxed and in normal posture comprises requesting the patient to walk in place prior to standing still.

The method in accordance with a preferred embodiment of the present invention, wherein the step of scanning comprises automatically recognizing the markers and the reference marker points in the digital images using a computer.

The method in accordance with a preferred embodiment of the present invention, wherein the computer comprises a user interface and, when the computer recognizes too many or too few of the markers, input is accepted via the user interface to remove or add, with reference to the digital images, the position coordinates of the markers which the computer incorrectly recognized or failed to recognize.

In accordance with the present invention, there is provided a method for calculating postural deviation values in a patient comprising the steps of:

a) obtaining position data identifying a position in space of body segments of the patient while standing relaxed and in normal posture, the body segments comprising head-shoulders, shoulders-pelvis, pelvis-hips, hips-knees and knees-ankles;

b) obtaining height and weight data of the patient;

c) calculating vertical and horizontal plumb lines using the position data;

d) calculating for at least some of the body segments an angle of deviation value and distance of deviation value with respect to the plumb lines using the position data.

The method in accordance with a preferred embodiment of the present invention, wherein the angle and distance of deviation values are referenced with respect to average or normal values.

The method in accordance with a preferred embodiment of the present invention, further comprising a step of calculating an effective weight or stress of at least one of the body segments using an estimated weight of the at least one body segment and the deviation values.

The method in accordance with a preferred embodiment of the present invention, wherein the deviation values are calculated for all of the body segments.

In accordance with the present invention there is provided a method of selecting exercises for improving tonicity and correcting posture in a patient, the method comprising the steps of:

a) obtaining biomechanical position data of the patient while standing relaxed and in normal posture, the position data indicative of postural problems requiring correction;

b) ranking the postural deviations by severity and priority;

c) correlating the position data with exercises for strengthing or stetching specific muscles or muscle groups to obtain ranking data for the exercises;

d) compiling an exercise program for the patient based on the ranking data.

The method in accordance with a preferred embodiment of the present invention, wherein the step of compiling comprises manually selecting exercises from a ranked list of exercises.

The method in accordance with a preferred embodiment of the present invention, wherein the exercises are grouped in sets of exercises each attempting to correct a specific postural deviation, the step of correlating comprising correlating the position data with the sets of exercises, and the exercise program comprising a series of the sets of exercises.

The method in accordance with a preferred embodiment of the present invention, wherein the exercises are grouped in sets of exercises each attempting to correct a specific postural deviation, the step of correlating comprising correlating the position data with the sets of exercises, and the exercise program comprising a series of the sets of exercises.

The method in accordance with a preferred embodiment of the present invention, wherein the position data identifies a position in space of body segments of the patient, the body segments comprising head-shoulders, shoulders-pelvis, pelvis-hips, hips-knees and knees-ankles, and the step of correlating comprises:

a) calculating vertical and horizontal plumb lines using the position data;

b) calculating for at least some of the body segments an angle of deviation value and distance of deviation value with respect to the plumb lines using the position data;

c) comparing the deviation values to normal values for the at least some of the body segments to obtain deviation priority values;

d) ranking the deviation priority values according to an order of severity or importance; and e) determining the ranking data based on an association of the exercises with body segment deviations in accordance with the order of severity or importance.

The method in accordance with a preferred embodiment of the present invention, wherein the step of ranking the deviation priority values according to an order of severity or importance comprises manually selecting deviations to be corrected by the exercise program, the order of severity or importance reflecting those deviations manually selected.

The method in accordance with a preferred embodiment of the present invention, wherein the exercises are grouped in sets of exercises each attempting to correct a specific postural deviation, and the exercise program comprising a series of the sets of exercises.

The method in accordance with a preferred embodiment of the present invention, wherein the exercise program is limited to a maximum number of exercises, the step of manually selecting deviations is automatically restricted when a maximum number of exercises corresponding to the selected deviations exceeds the maximum number for the exercise program.

The method in accordance with a preferred embodiment of the present invention, wherein the step of compiling comprises repeating ones of the exercises corresponding to most severe postural problems regularly throughout the exercise program and including ones of the exercises corresponding to less severe postural problems for only part of the program.

The method in accordance with a preferred embodiment of the present invention, wherein the step of compiling comprises including ones of the exercises corresponding to moderately severe postural problems more intensively for only part of the exercise program.

The method in accordance with a preferred embodiment of the present invention, wherein the step of compiling comprises repeating ones of the exercises corresponding to most severe postural problems regularly throughout the exercise program and including ones of the exercises corresponding to less severe postural problems for only part of the program.

The method in accordance with a preferred embodiment of the present invention, wherein the step of compiling comprises including ones of the exercises corresponding to moderately severe postural problems more intensively for only part of the exercise program.

The method in accordance with a preferred embodiment of the present invention, further comprising steps of:
  a) obtaining, after completing of the exercise program, new biomechanical position data of the patient while standing relaxed and in normal posture;
  b) evaluating an effectiveness of the exercises in the exercise program for correcting the postural problems; and
  c) adjusting parameters used in the step of correlating for future patients based on the effectiveness evaluated in the previous step.

The method in accordance with a preferred embodiment of the present invention, wherein the exercise program is repeatedly varied until the effectiveness of the exercises is optimized.

The method in accordance with a preferred embodiment of the present invention, wherein the steps of correlating, evaluating and adjusting are carried out using a centralized shared database of the parameters used in the step of correlating for a large number of patients.

The method in accordance with a preferred embodiment of the present invention, wherein the parameters include at least one of an age and an activity level of the patient.

In accordance with the present invention there is provided a method of providing posture health care using a distributed system, the method comprising the steps of:
  a) obtaining personal data of a patient, the personal data including weight, height, gender and activity data of the patient, and obtaining posture anatomical reference position data of the patient at a biomechanical measurement station;
  b) processing the personal and position data using data stored in a remote central database to obtain preliminary postural deviation assessment data;
  c) providing the preliminary postural deviation assessment data to one of a health-care practitioner and the patient;
  d) obtaining corrected postural deviation assessment data from one of the health-care practitioner and the patient; and
  e) modifying the data stored in the central database using the corrected data.

The method in accordance with a preferred embodiment of the present invention, wherein the preliminary postural deviation assessment data comprises a ranked list of deviations and a preliminary selection of the deviations to be included in a therapeutic exercise program, and the corrected data comprises a corrected selection of the deviations to be included in a therapeutic exercise program.

The method in accordance with a preferred embodiment of the present invention, wherein:
  the preliminary postural deviation assessment data comprises a set of therapeutic exercises of an exercise program;
  the corrected data comprises new posture anatomical reference position data of the patient obtained after completion of the exercise program; and
  step (e) comprises processing the new reference position data to determine an effectiveness of the therapeutic exercises in correcting postural deviations and modifying accordingly the data stored in the central database.

The method in accordance with a preferred embodiment of the present invention, wherein:
  step (a) comprises validating completeness of the reference position data at the biomechanical measurement station and transmitting the personal and position data to a central server;
  step (b) is a carried out at the central server;
  step (c) comprises transmitting the preliminary postural deviation assessment data from the central server to one of the health-care practitioner and the patient;
  step (d) comprises transmitting the corrected data to the central server; and
  step (e) is carried out by the central server.

The method in accordance with a preferred embodiment of the present invention, wherein the biomechanical measurement station includes a health-care practitioner client station in communication with the central server.

The method in accordance with a preferred embodiment of the present invention, wherein the client station uses a web browser interface to communicate with the central server, the central server providing a secure connection to a biomechanical assessment report web document for the patient.

For the purpose of the present invention the following terms are defined below.

The term "anterior view" is intended to mean the view of the front of the body (with the person in anatomical position). The term "lateral view" is intended to mean the view of the patient from the side.

The term "posterior view" is intended to mean the view of the patient from behind.

The term "body segment parameters" is intended to mean the spatial coordinates of body segments and key anatomical landmarks taken from the images from the lateral, anterior and posterior views.

The present invention provides a process and apparatus to acquire patient images rapidly and accurately in a clinical environment, to extract body segment parameters from surface markers, a method for analysing these data to obtain biomechanical parameters and deviations, a method involving the use of these biomechanical parameters and deviations for the detection of postural deviations and the selection of corrective exercices, and the use of Internet to provide a distributed system for patient care involving image acquisition in a clinical environment, data analysis at a central server and communication between the central server and the health-care professional as well as potential follow-up and feedback between the patient and either the health-care professional or the central server or both. The placement of markers based on a well established model of ideal postural alignment is crucial because the placement of markers determines the relative deviation of body segments from vertical and horizontal "plumb" or ideal alignment. The current system uses the most widely used and respected anatomical definition of ideal postural alignment (Kendall, McCreary, & Provance, 1993). And, a sophisticated marker placement system has been designed to place surface markers on locations defining this alignment. The importance of a correct definition of ideal posture is obvious when one is attempting to detect postural deviations. A further crucial difference between the earlier systems and the present invention is the use of scanning technology to automatically detect the location of reflective markers placed on the skin overlying skeletal landmarks. They can be placed directly on the skin because they are made from a hypoallergenic material. Such marker placement is highly important, because it avoids the potential examiner error associated with the manual identification of presumed skeletal landmarks from video images. The current system automatically detects markers, and their locations are transmitted automatically through the web for the calculation of postural deviations. Further differences between earlier state of the art and the current system includes the automatic generation of a personalized exercise plan based on individualized and automatic assessments of patients' biomechanical and postural status.

As such, the biomechanical knowledge system radically changes the practice of biomechanical analysis by creating an objective and effective methodology that is simple to implement using complex yet innovative technology. We have developed a strong theoretical model of biomechanical function as well as innovative methods for data capture, analysis and adapted exercise routines. Both theoretical and technological aspects of our system have been integrated into a coherent and operational system.

We have successfully linked a biomechanical assessment of potential postural deviations to the underlying muscular components giving rise to these deviations. We go further by suggesting specific muscular training routines to ameliorate the underlying muscular and postural deviations. This unique theoretical and methodological link will be outlined in more detail below.

BRIEF DESCRIPTION OF THE DRAWINGS

Having thus generally described the nature of the invention, reference will now be made to the accompanying drawings, showing by way of illustration a preferred embodiment thereof, and wherein:

FIG. 1: surface anatomical marker locations in the anterior view;

FIG. 4: the retroreflective marker sticker construction according to the preferred embodiment;

FIG. 5: the retroreflective marker sphere and application sticker assembly according to the preferred embodiment;

FIG. 12: description of missing marker calculation;

FIG. 13: page of the Biomechanical Assessment Report (Biomechanical Assessment Report) with patient's image, deviations and biomechanical parameters;

FIG. 14: page from the Biomechanical Assessment Report with postural deviations and associated exercises and stretching;

FIG. 15: page from the Biomechanical Assessment Report with exercise schedule; and FIG. 16: page from the Biomechanical Assessment Report with illustration and description of two of the many possible exercises of the exercise program

DETAILED DESCRIPTION OF THE INVENTION

Figure 2B:
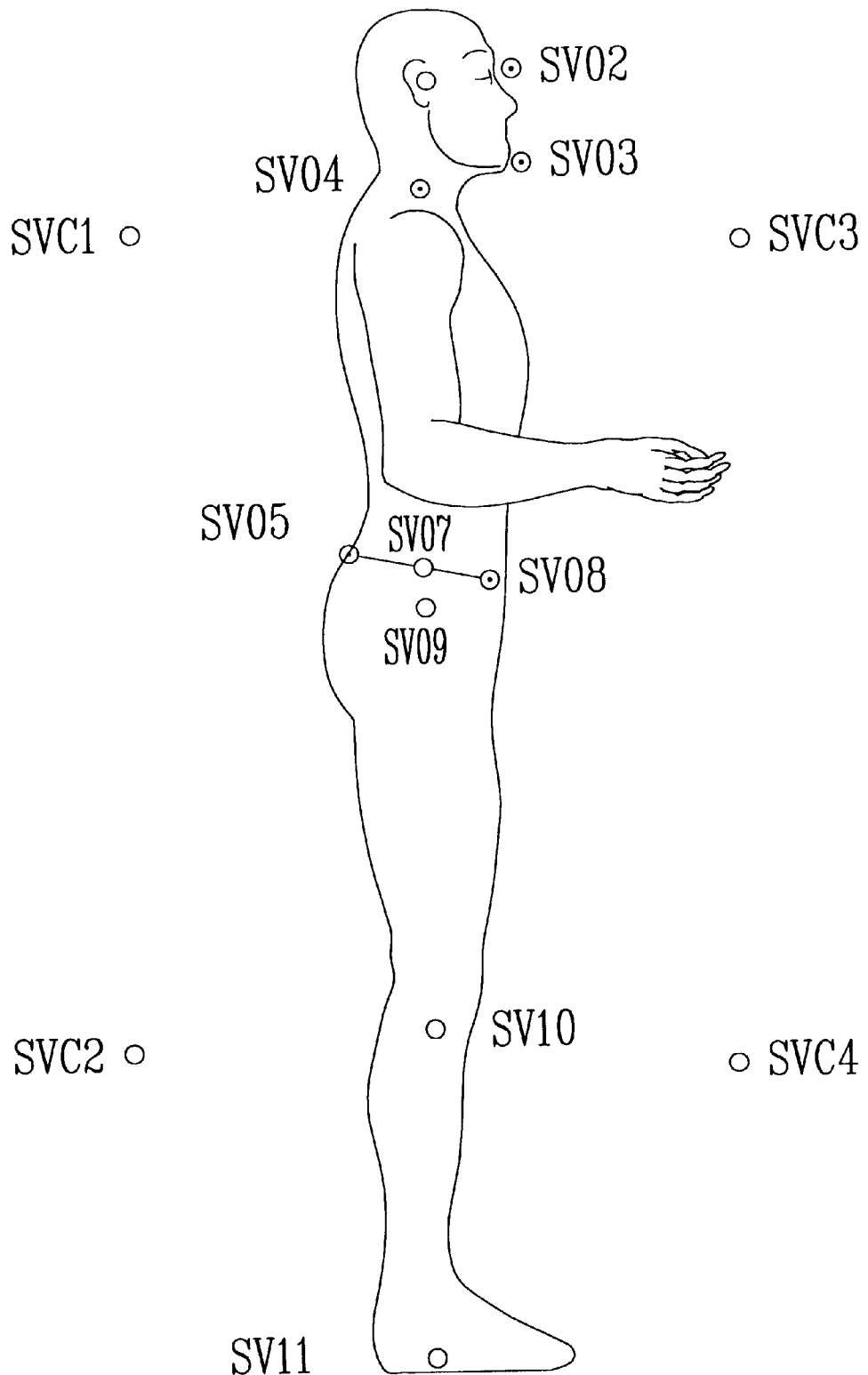
FIG. 2: marker positions in the lateral view.

In accordance with the present invention, there is provided a system and method using biomechanical analysis to generate a schedule of corrective exercises suitable for a patient's condition.

The present invention follows the established biomechanical and clinical principle that resting, standing posture is a composite state made up of the relative position of body segments (e.g., head, trunk, legs) in space and relative to gravity. This is known as static postural alignment. Posture can also be described in terms of muscular balance. Proper posture is the result of symmetrical muscular development and the appropriate interaction of flexor and extensor muscles in a way that suits a vertical stance.

The method described in the present application is based on hypotheses underlying muscular balance, such hypotheses being that:

All alignment problems yield abnormal tension and constrain the skeleton, joints, ligaments and muscles.

The study of the relative position of linked body segments reveals muscles that are hyper- or hypo-contracted.

Alignment and muscular balance are correlated for normal posture.

Muscular imbalance promotes an increase in the distance of a body segment from correct vertical and horizontal alignment.

Depending on the deviation, antagonist muscle groups must be strengthened or stretched to achieve correct muscular balance and postural change.

The inseparable qualities that are alignment and muscular balance are central components of correct body mechanics. A correct vertical stance is the result of a harmonious combination of joint and body segment positions, which in turn stem from an optimal ratio of agonist/antagonist muscles. The energy expenditure required by the muscles is minimal. Therefore, there is an optimal alignment of the body that must take into account all anatomical structures involved in maintaining this alignment. Further, alignment is maximal when the load-bearing structures are also positioned optimally relative to gravity. The sum of forces that act on anatomical structures are balanced if the body is correctly positioned. Daily activities and habits often transform the body from ideal postural alignment independently of disease or structural anomalies. This can have highly negative consequences on daily living, and particularly in terms of the energy necessary to maintain the disordered posture and overlying movements. It is therefore very important to identify and correct these postural deviations.

The following steps are involved in the postural assessment-postural deviation muscular identification-exercise process. These steps consists of:

Comprehensive biomechanical analysis

Identification of postural deviations and ranking by order of priority

Specification of muscular factors underlying the postural deviations

Personalised muscular stretching and exercises routines to ameliorate postural deviations that incorporates level of difficulty and order of priority of deviations Assessment of client progress by follow-up Biomechanical Assessment Reports and Modification of exercise protocol, if necessary.

The marker construction according to the preferred embodiment is illustrated in FIGS. 4 and 5. There are two types of markers, flat round disks 25 and spheres 30. The disks 25 and spheres 30 share the same diameter, namely about 2 cm. The spherical and flat markers are placed on the surface of a patient's body using hypoallergenic adhesive, the markers being placed over skeletal landmarks that define ideal postural alignment. The skeletal landmarks used in the present invention are landmarks which have been recommended by the teachings of Kendall et al. (1993) mentioned above. The adhesive layer 21 is provided on a release sheet 20 with a lift-off tab 24. The retroreflective disk 25 is already attached to the adhesive sheet 22 which has the same shape as the disk, except for the tab 24. Due to the double-sided adhesive sheet 22, the adhesive layer 21 is hypoallergenic and is used to contact the skin or the tight clothing of the patient 36, while the adhesive layer 23 allows the disk 25 to be held in place or peeled off. When the disk 25 is peeled off, the sheet 22 remains adhered to the patient surface 36, and exposes the layer 23. The sphere 30, having a truncated flat side is adhered to layer 23, and is thus applied to patient surface 36. The sphere 30 comprises a wooden Core 32 which is dipped in a retroreflective paint (Axon Alert 1460, Axon Aerospace, Greenville, U.S.A.) which forms a coating 34.

The disk 25 is cut from stock sheet of retroreflective material made by 3M, namely 3929 Thermal Transfer Printable Retro-Reflective Label Stock and has a thickness of 3 mm. The double-sided adhesive sheet 22 is made by 3M, namely 1522, Double Coated Medical Tape. The adhesive layers 21 and 23 are hypoallergenic, pressure sensitive acrylate adhesive. The coating material 34 comprises 85% solids per weight and the fineness of grind is 200 mesh. The mixing and coating process is as follows. Surfaces to be paint are cleanned and lightly abraded before coating. The spheres are then dipped between 2 to 5 minutes and dryed under normal drying conditions.

Four digital images are taken of the patient using camera 10 in order to provide a visual image of postural alignment for the patients and health-care professionals and for the automatic detection of body segment parameters. The camera 10 has a standard built-in flash 12 which is set to operate during image acquisition. The intense light form the flash is reflected by the markers 25 and 30 and the markers appear as bright small circles in the acquired images. The high contrast of the markers 25 and 30 with respect to the image of the patient facilitates later automatic recognition of the markers. The placement of markers in the anterior view is shown in FIG. 1. FA02 is a spherical marker placed on the glabella, FA03 is a spherical marker placed on the middle of the chin and overlying the mental protuberance, FA05 is a spherical marker placed on the right shoulder over the acromion, FA07 is a spherical marker placed on the left shoulder over the acromion, FA06 is a marker placed on the jugular notch, FA08 is a marker placed over the umbilicus, FA09 is a spherical marker placed on the right anteriosuperior iliac spine, FA11 is a marker placed on the left anterior superior iliac spine, FA12 is a marker placed on the right wrist over the styloid process of the radium, FA13 is a marker placed on the left wrest over the styloid process of the radius, FA14 is a marker centered over the right patella, FA15 is a marker centered over the left patella, FA16 is a marker centered between the right medial and lateral malleoli, FA18 is a marker centered between the left medial and lateral malleoli, FA19 is a marker placed on the anterior aspect of the right distal phalanx of the great toe and FA20 is a marker placed on the anterior aspect of the left distal phalanx of the great toe.

The markers on the lateral view are placed as shown in FIG. 2. SD01 is a marker placed on the tragus of the right ear, SD02 is a spherical marker placed on the glabella, SD03 is a spherical marker placed on the middle of the chin, and overlying the mental protuberance, SD04 is a spherical marker placed on the right shoulder over the acromion, SD05 is a spherical marker placed over the right posterior superior iliac spine, SD08 is a spherical marker placed on the right anteriosuperior iliac spine, SD09 is a marker placed over the greater trochanter, SD10 is a marker placed on Gerdy's tubercle and SD11 is a marker placed on the transverse tarsal joint.

Figure 3:
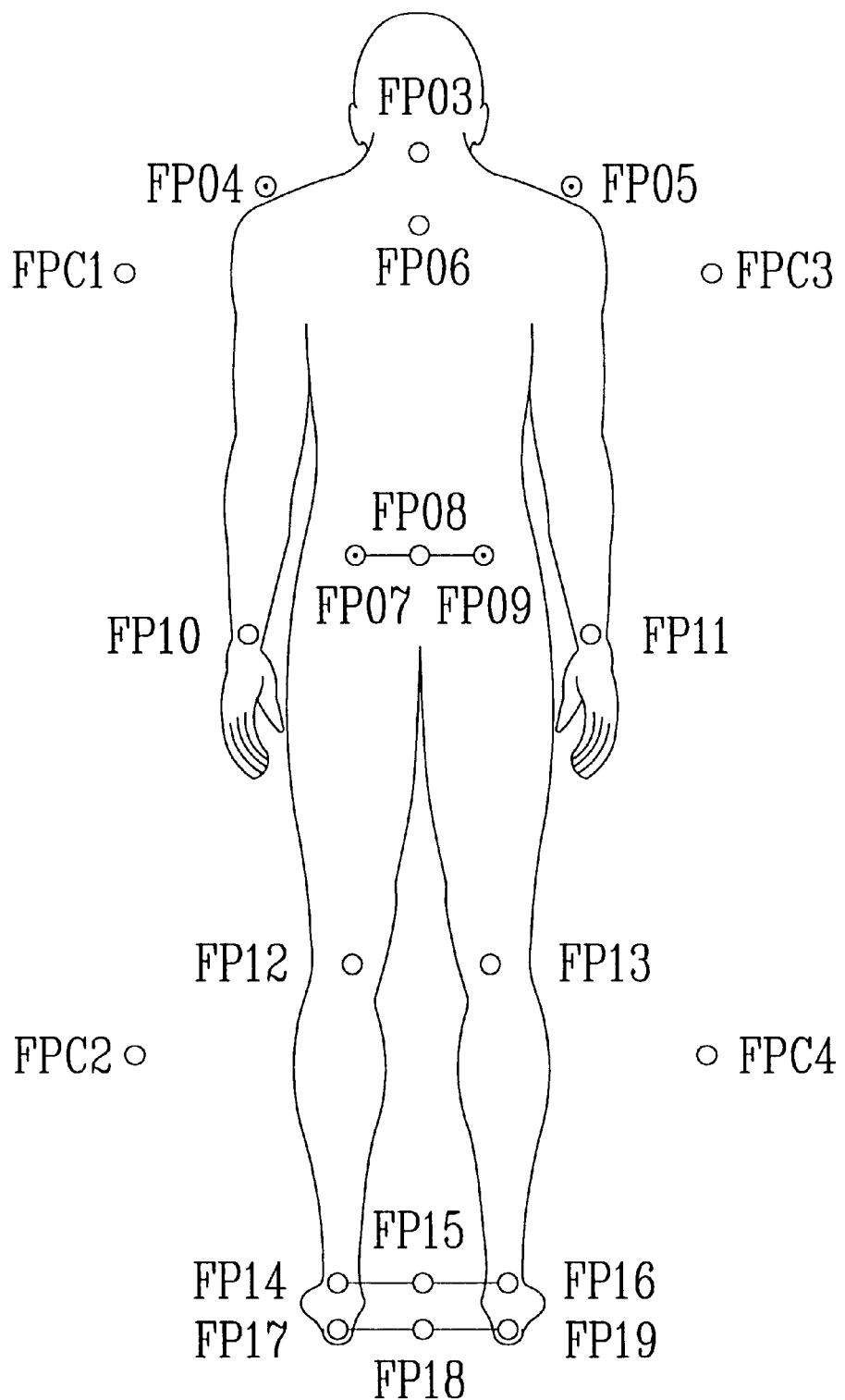
FIG. 3: marker positions in the posterior view.

The markers on the posterior view are placed as shown in FIG. 3. FP03 is a marker placed over the spinous process of the seventh cervical vertebra, FP04 is a spherical marker placed on the left shoulder over the acromion, FP05 is a spherical marker placed on the right shoulder over the acromion, FP06 is a marker placed over the spinous process of the fifth thoracic vertebra, FP07 is a marker placed over the left posterior superior iliac spine, FP08 is a spherical marker placed over the right posterior superior iliac spine, FP10 is a marker placed on the left wrist over the styloid process of the ulna, FP11 is a marker placed on the right wrist over the styloid process of the ulna, FP12 is a marker placed over the center of the left popliteal cavity, FP13 is a marker placed over the center of the right popliteal cavity, FP14 is a marker centered over the left Achilles tendon at the level of the medial malleolus, FP16 is a marker centered over the right Achilles tendon at the level of the medial malleolus, FP17 is a marker centered over the calcaneous of the left foot and FP19 is a marker centered over the calcaneous of the right foot.

Precise position of the markers is essential for accurate biomechanical assessment and detection of postural deviations. For this, the patient must wear very tight workout clothes to avoid hiding the few landmarks that are potentially covered by clothing. Most markers are placed directly over the body surface. The health-care practitioner must palpate the patient to make sure that the markers are well positionned.

Figure 6:
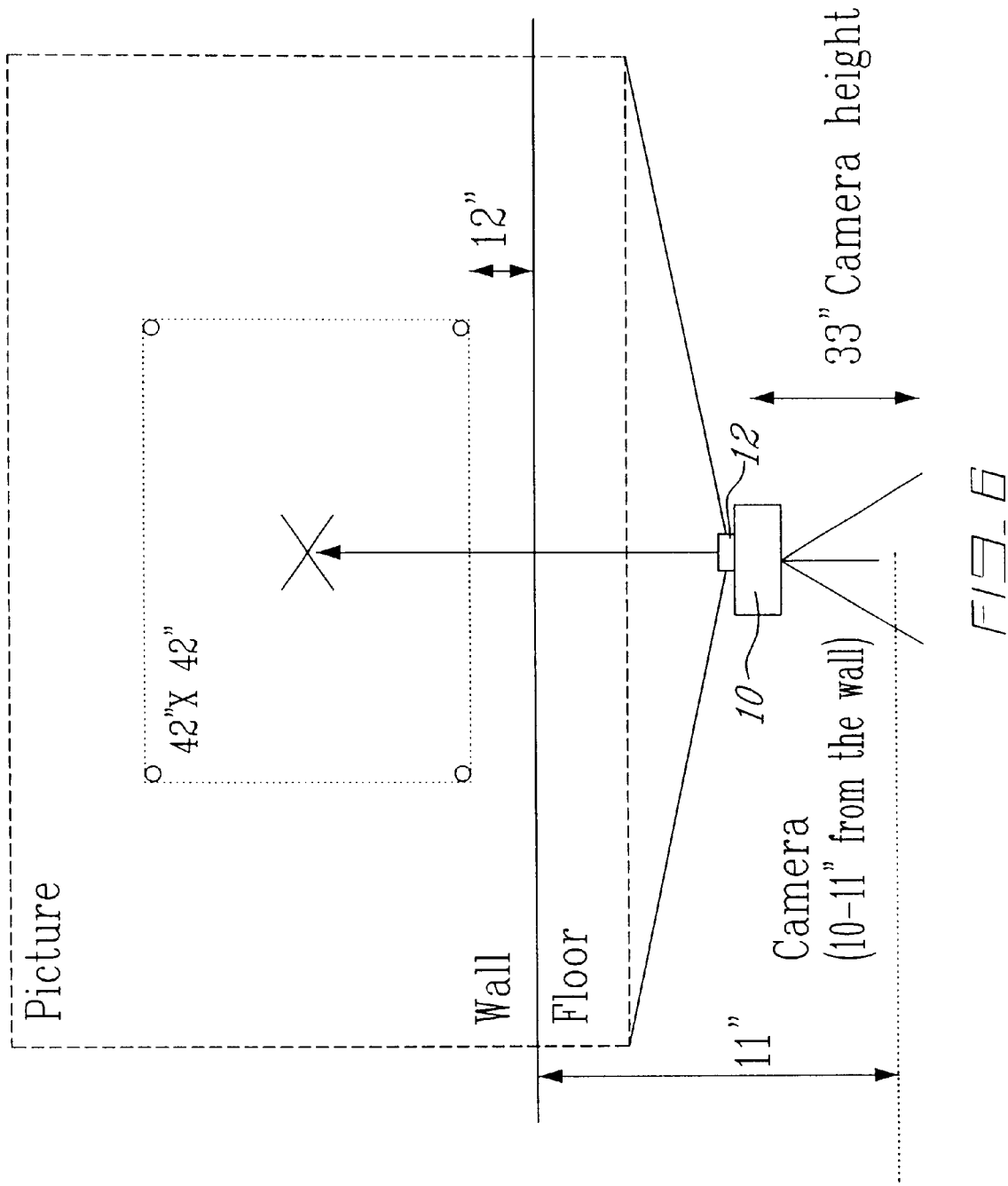
FIG. 6: the position of the camera and calibration backdrop.
Figure 11:
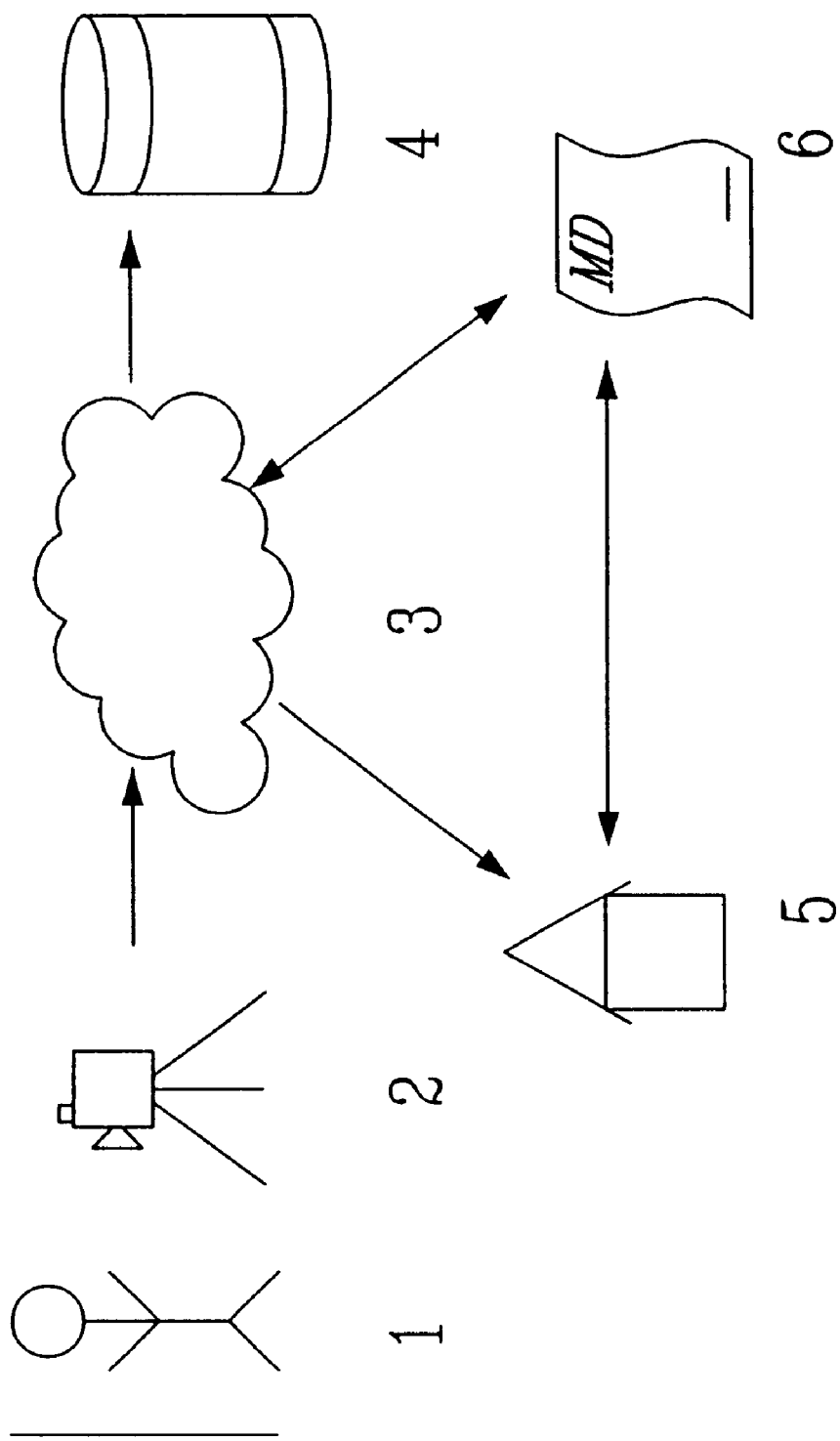
FIG. 11: the schema server-user.

Shown in FIGS. 6 and 11 is the position of the camera (2) and calibration backdrop and the data process. Pictures are taken with a flash to use the retroreflective property of the markers and make them more apparent on the pictures. The first picture is taken from the lateral view with arms down. The second picture is also from the lateral view but with the proximal arm flexed at 90° to detect the position of markers potentially hidden with the arm down. These values are eventually transferred to the more "natural" lateral image with the arm down. The third and fourth pictures are taken from the anterior and posterior views, respectively. The pictures are taken against a backdrop including a plurality of scale and orientation reference marker points facilitating body segment parameters calculation. Also the patient (1) is instructed to stand in a relaxed and normal posture. To help the patient to adopt the most natural body posture possible, the patient is asked to walk in place prior to standing still.

The digital Images are stored on a flash memory card within the camera and then transferred to a card reader connected to a computer which in turn, is connected to the Internet (3). The health-care professional (6) can then connect to the central processing server (4) of FIG. 11 entering on the system web site. First step, the health-care practitionner has to identify client. If the client has his or her first evaluation, personal data (height, weight, gender, age, activity level, preferred unit of measurement) is entered. A client identification number (5) is created to identify client data in the database but protect confidentiality. In the second step, the health-care professional starts the image scanning and biomechanical assessment process. The health-care practitioner select each patient's images in the directory on the computer. The positions of the anatomical markers that define body segments are scanned and coordinates sent via the Internet to the central server for processing. To protect patient privacy, the images themselves are never sent via the Web, only the coordinates of the markers are transferred.

The digital location of the markers is supplied and the system receives the scan, validates it and sends back a validation message to the health-care practitioner. The health-care professional receives an error message if insufficient or excessive markers are apparent in the automatic scan. A manual function is provided to correct marker placements, if necessary, and the images are re-scanned. If it is determined that the marker position data obtained from the images is flawed, the health-care professional may again acquire the images, possibly after rechecking the marker positioning. As will be appreciated, when the imaging is complete, and after confirming that the marker positions have been validated, the tabs 24 of the adhesive sheets 22 for the markers 25 and 30 facilitate removal of the adhesive sheets from the clothing or skin 36 of the patient (see FIG. 5). Since a large number of markers needs to be removed, saving time in their removal allows the patient to finish up quicker and change back into his or her clothes.

The next step is to update credit information, submit it to the system and confirm payment. The system sends back a validation message to the health-care practitioner to proceed.

Further to that step, biomechanical calculations are executed on the central server (4) of the FIG. 11.

The first step is the conversion of images from pixels to actual distances. To do so, the origin is redefined as follow:

$$x' = x - \frac{w}{2}$$

$$y' = \frac{h}{2} - y$$

where
  w=image width and
  h=image height

Then the image rotation is proceed as follow:

$$dx = \left(\frac{C1x - C2x}{2}\right) + \left(\frac{C3x - C4x}{2}\right)$$

$$dy = \left(\frac{C1y - C2y}{2}\right) + \left(\frac{C3y - C4y}{2}\right)$$

$$x'' = x'\frac{dy}{d} - y'\frac{dx}{d}$$

$$y'' = y'\frac{dy}{d} - x'\frac{dx}{d}$$

where $$d = \sqrt{dx^2 + dy^2}$$

with C1, C2, C3 and C4 being calibration points from the backdrop.

Figure 7:
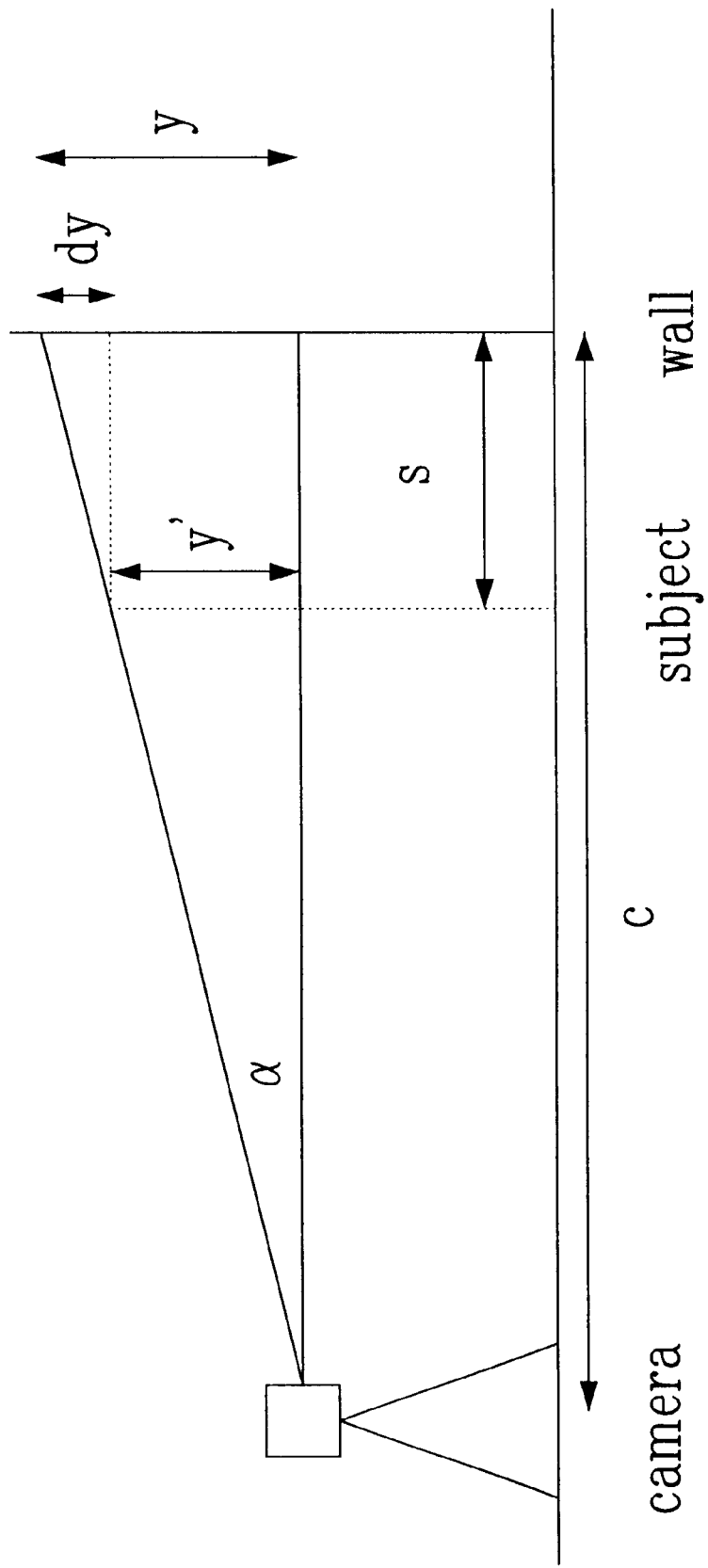
FIG. 7: the perspective of the subject relative to the wall and the camera, as well as measures used for calculations.
Figure 8:
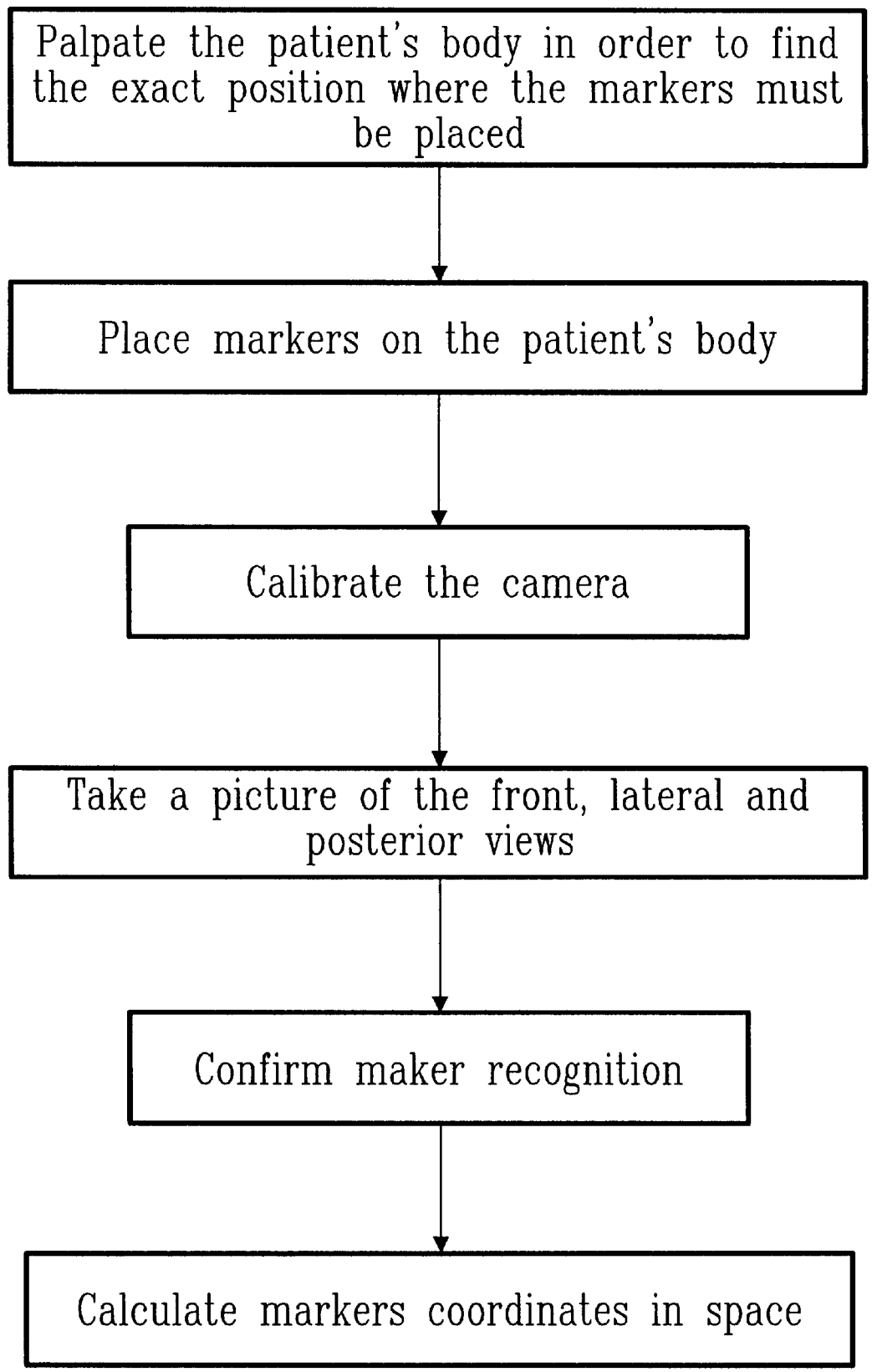
FIG. 8: the flowchart describing the image acquisition and the obtention of the location of anatomical markers.
Figure 9:
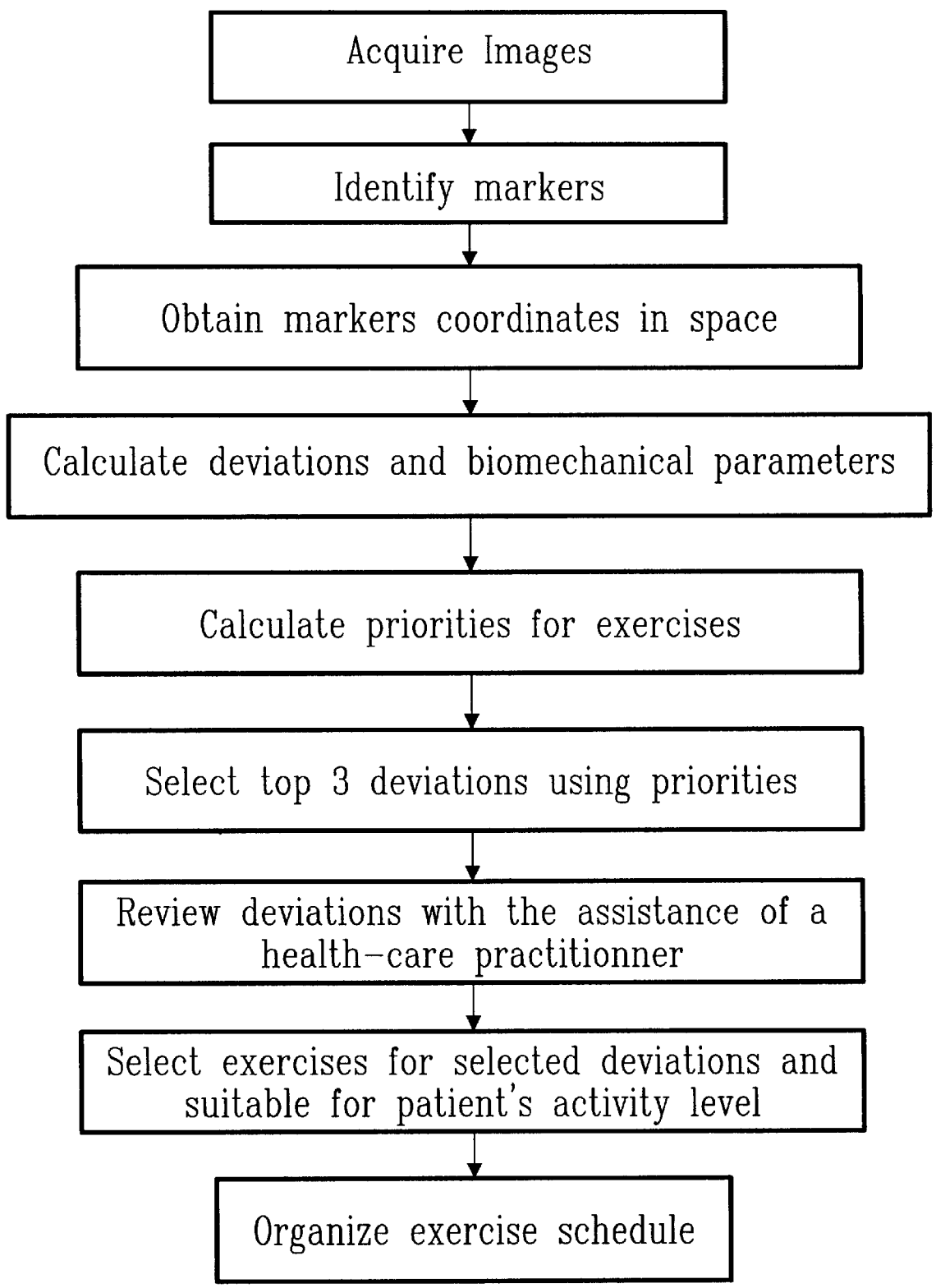
FIG. 9 shows the flowchart describing the process to generate an exercise schedule.
Figure 10:
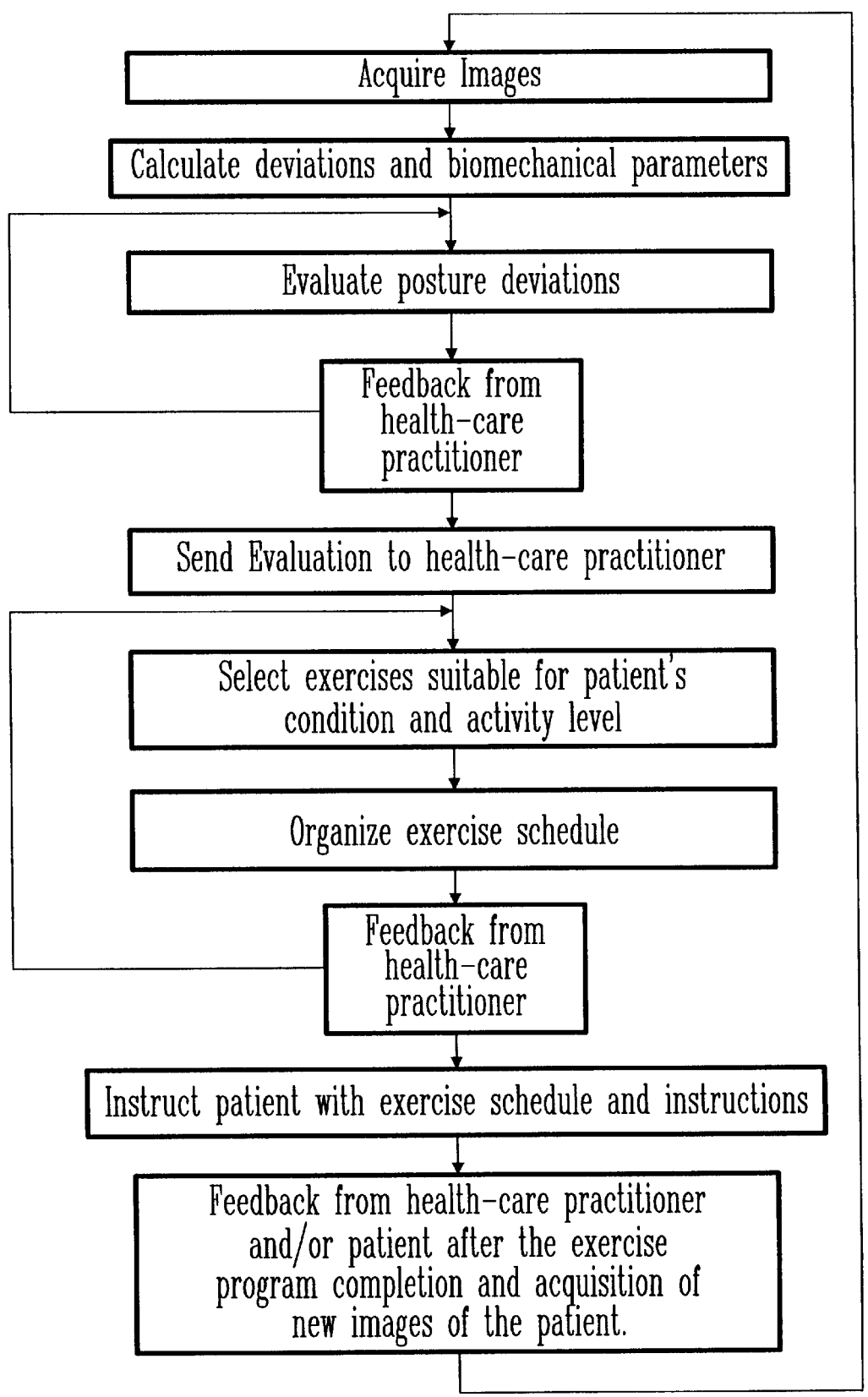
FIG. 10: the flowchart describing the overall process of biomechanical assessment, postural deviation detection, exercise generation, feedback from health-care practitioner to patient and follow-up.

With these calculations it is possible to get coordinate values of the position of anatomical markers relevant to plumb lines in millimeters (or inches with conversion). Shown in FIG. 7 is the perspective needed for this process.

D=Calibration dimension (mm)
c=distance of camera from the wall
s=distance of the subject from the wall $$D' = D\left(1 - \frac{s}{c}\right)$$

$$x''' = \frac{D'}{d}\left(x'' + \frac{w}{2}\right)$$

$$y''' = \frac{D'}{d}\left(y'' + \frac{h}{2}\right)$$

The calculation of (1−s/c) is obtained with the following formulas:

$$\tan(\alpha) = \frac{dy}{s} = \frac{y}{c}$$

$$dy = \frac{y \times s}{c}$$

$$Y' = y - dy$$

$$y' = y\left(1 - \frac{s}{c}\right)$$

The same calculations may be made with respect to x and the distance d' can be calculated as:

$$d' = d\left(1 - \frac{s}{c}\right)$$

The calculations made, the coordinates of markers are determined and expressed relative to vertical and horizontal plumb lines. The missing markers positioned in pelvic area are then calculated. Shown below are the equations used to determine marker coordinates and FIG. 12 displays the missing markers on the pelvis area. SD5, SD8, SV5 and SV8 represent the markers on the pelvic area. d is the segment relating SD5 and SD8 and b is the segment relating SD5 and SD9. The angle θ is the angle between the markers SD5 and SD8. In reconstructing a right-angle triangle where d is the hypotenuse, w is the leg facing the hypotenuse and h is the remaining leg of the rectangle.

Plus: FA9(x2", y2") and FP9(x1", y1")

$dx=(x2'-x1')$ $bx=(x3'-x1')$ $dy=(y2'-y1')$ $by=(y3'-y1')$ $h=(y2''-y1'')$ $d=\sqrt{dx^2+dy^2}$ $b=\sqrt{bx^2+by^2}$ $\vec{d} \cdot \vec{b} = db \cos\theta = dxbx + dyby$ $\theta = \cos^{-1}\left(\frac{dxbx + dyby}{db}\right)$ $d^2=(x2-x1)^2+h^2$ $x2=x1+\sqrt{d^2-h^2}$ or $x1=x2-\sqrt{d^2-h^2}$ $y2=y1+h$ or $y1=y2-h$ $w=x2-x1$ $x3 = x1 + \frac{b}{d}(w\cos\theta - h\sin\theta)$ $y3 = y1 + \frac{b}{d}(h\cos\theta + w\sin\theta)$ Marker coordinates are used in the next step to determine a patient's deviations from optimal alignment. Shown in Table 1 are the calculations necessary to determine postural deviations.

TABLE 1

| Code | Related body parts | Formula | Units |
|---|---|---|---|
| FA_ANG1 | Shoulders | ARCTAN((FA07Y − FA05Y)/(FA07X − FA05X)) | ° |
| FA_ANG2 | Pelvis | ARCTAN((FA11Y − FA09Y)/(FA11X − FA09X)) | ° |

TABLE 1-continued

| Code | Related body parts | Formula | Units |
|---|---|---|---|
| FA_ANG3 | Knees | ARCTAN((FA15Y − FA14Y)/(FA15X − FA14X)) | ° |
| FA_DIST1 | Shoulders | ((FA05X + FA07X)/2) − FA17X | mm |
| FA_DIST2 | Forehead | FA02X − FA17X | mm |
| FA_DIST3 | Navel | FA08X − FA17X | mm |
| FA_DIST4 | Pelvis | FA10X − FA17X | mm |
| FA_DIST5 | Knees | ((FA14X + FA15X)/2) − FA17X | mm |
| FA_DIST6 | Toes | ((FA20X + FA19X)/2) − FA17X | mm |
| FP_ANG_AN1 | Left Foot | ARCTAN((FP14X − FP17X)/(FP14Y − FP17Y)) | ° |
| FP_ANG_AN2 | Right foot | ARCTAN((FP16X − FP19X)/(FP16Y − FP19Y)) | ° |
| FP_ANG1 | Shoulders | ARCTAN((FP05Y − FP04Y)/(FP05X − FP04X)) | ° |
| FP_ANG2 | Pelvis | ARCTAN((FP09Y − FP07Y)/(FP09X − FP07X)) | ° |
| FP_ANG3 | Knees | ARCTAN((FP13Y − FP12Y)/(FP13X − FP12X)) | ° |
| FP_DIST1 | Shoulders | ((FP04X+FP05X)/2) − FP18X | mm |
| FP_DIST2 | 7th cervical | FP03X − FP18X | mm |
| FP_DIST3 | 5th dorsal | FP06X − FP18X | mm |
| FP_DIST4 | Pelvis | FP08X − FP18X | mm |
| FP_DIST5 | Knees | ((FP13X + FP12X)/2) − FP18X | mm |
| FP_DIST6 | Ankles | FP15X − FP18X | mm |
| SD_ANG1 | Head-Shoulders | ARCTAN((SD01X − SD04X)/(SD04Y − SD01Y)) | ° |
| SD_ANG2 | Shoulders-Pelvis | ARCTAN((SD04X − SD07X)/(SD07Y − SD04Y)) | ° |
| SD_ANG3 | Pelvis-Hips | ARCTAN((SD07X − SD09X)/(SD09Y − SD07Y)) | ° |
| SD_ANG4 | Hips-Knees | ARCTAN((SD10X − SD09X)/(SD09Y − SD10Y)) | ° |
| SD_ANG5 | Knees-Ankles | ARCTAN((SD11X − SD10X)/(SD10Y − SD11Y)) | ° |
| SD_DIST1 | Head | SD01X − SD11X | mm |
| SD_DIST2 | Shoulders | SD04X − SD11X | mm |
| SD_DIST3 | Pelvis | SD07X − SD11X | mm |
| SD_DIST4 | Hips | SD09X − SD11X | mm |
| SD_DIST5 | Knees | SD10X − SD11X | mm |

Deviations from horizontal and vertical alignment, moments of force and reaction forces, and center of gravity are calculated from the biomechanical parameters obtained from the images in the lateral, anterior and posterior views. The deviation values are referenced with respect to body alignment position values. These values are used both in the detection of postural deviations and also as a follow-up tool to assess patient progress after following a corrective exercise plan.

These values are used as a diagnostic tool and as a way to measure progress in the patient's condition.

Constants:

Head Ratio: RaH=8.4%

Trunk Ratio: RaT=58.4%

Gravity: G=9.8 m/s$^2$

Global:

Weight Total: We=Total person mass (kg)

Weight head: WeH=We*RaH*G

Weight trunk: WeT=We*RaT*G

Weight head&trunk: WeHT=WeH+WeT

Lateral Plane:

Angle Head: $LAnHA = A\text{Tan}\left(\dfrac{SD01X - SD04X}{SD04Y - SD01Y}\right)$ Moment Head: $LMoH = \dfrac{WeH*(SD01X - SD04X)}{1000}$ Reaction Head: $LReH = -LMoH*25 - WeH$ Reaction Head %: $\text{Abs}\left(\dfrac{LReH}{WeH}\right)$ Angle Trunk: $LAnTI = A\text{Tan}\left(\dfrac{SD04X - SD07X}{SD07Y - SD04Y}\right)$ Moment Trunk: $LMoT = \dfrac{WeT*(SD04X - SD07X)}{1000}$ Reaction Trunk: $LReT = -LMoT*20 - WeHT$ Reaction Trunk %: $LReTP = \text{Abs}\left(\dfrac{LReT}{WeT}\right)$ Angle Head&Trunk: $LAnHA = A\text{Tan}\left(\dfrac{SD01X - SD07X}{SD07Y - SD01Y}\right)$ Moment Head&Trunk: $LMoHT = \dfrac{WeHT*(SD01X - SD07X)}{1000}$ Reaction Head&Trunk: $LReH = -LMoHT*20 - WeHT$ Reaction Head&Trunk %: $LReHTP = \text{Abs}\left(\dfrac{LReHT}{WeHT}\right)$ Front Plane:

Angle Head: $LAnHA = A\text{Tan}\left(\dfrac{FA02X - FA06X}{FA06Y - FA02Y}\right)$ Moment Head: $LMoH = \dfrac{WeH*(FA06X - FA02X)}{1000}$ Reaction Head: $LReH = -LMoH*25 - WeH$ Reaction Head %: $\text{Abs}\left(\dfrac{LReH}{WeH}\right)$ Angle Trunk: $LAnTI = A\text{Tan}\left(\dfrac{FA06X - FA10X}{FA10Y - FA06Y}\right)$ Moment Trunk: $LMoT = \dfrac{WeH*(FA10X - FA06)}{1000}$ Reaction Trunk: $LReT = -LMoT*20 - WeT$ Reaction Trunk %: $LReTP = \text{Abs}\left(\dfrac{LReT}{WeT}\right)$ Angle Head and Trunk: $LAnHTI = A\text{Tan}\left(\dfrac{FA02X - FA10X}{FA10Y - FA02Y}\right)$ Moment Head and Trunk: $LMoHT = \dfrac{WeHT*(FA10X - FA02X)}{1000}$ Reaction Head and Trunk: $LReHT = -LMoHT*20 - WeHT$ Reaction Head and Trunk %: $\text{Abs}\left(\dfrac{LReHT}{WeHT}\right)$ The center of gravity projection is calculated as follows:
The center of gravity projection is calculated as follows:
X coordinates: ((FA17X−(FA02X+FA04X)/2)*WeFAH+ (FA17X−(FA07X+FA05X)/2)*WeFAS+(FA17X−(FA11X+ FA09X)/2)*WeFAP+(FA17X−(FA14X+FA15X)/2) *WeFAK)/(WeFAH+WeFAS+WeFAP+WeFAK)
Y coordinates: ((SD11X−SD01X)*WeSDH+(SD11X− SD04X)*WESDS+(SD11X−SD07X)*WeSDP+(SD09X− SD10X)/SQRT((SD10Y−SD09Y)^2+(SD09X−SD10X)^2) *RATIO_SD_THIGH_LENGTH*Height*WeSDT+ (SD10X−SD11X)/ SQRT((SD11Y−SD10Y) ^2+(SD10X− SD11X) ^2)*RATIO_SD_LEG_ LENGTH*Height*WeSDK)/(WeSDH+WeSDS+WeSDP+ WeSDT+WeSDK)

Where the parameters used to calculate the center of gravity are described herewith:

| Parameters | Description | View |
|---|---|---|
| WeFAH | Head weight | Anterior |
| WeFAS | Shoulder weight | Anterior |
| WeFAP | Pelvis weight | Anterior |
| WeFAK | Segment weight (whole leg) | Anterior |
| WeSDH | Head weight | Lateral |
| WeSDS | Shoulder weight | Lateral |
| WeSDP | Pelvis weight | Lateral |
| WeSDT | Thigh weight | Lateral |
| WeSDK | Segment weight (knee to foot) | Lateral |
| Ratio_SD_Thigh_Length | Center of mass for the thigh in % of the segment length | Lateral |
| Ratio_SD_Leg_Length | Center of mass for the leg (knee to foot) in % of the segment length | Lateral |

These coordinates are then compared to the ideal center of gravity position located on the base of support between the feet.

When the Biomechanical Assessment is complete (a virtual instantaneous process through the central server), data are transferred back to the health-care practitioner's computer via the Web. A Biomechanical Assessment Report can then be generated and modified as needed. The health-care practitioner has the possibility to adjust postural deviations based on supplemental information that he or she may have noted during the patient's examination. Postural deviations are ranked automatically and based on the relative importance of the trunk and head and neck stability on postural function. The top three deviations are selected by default for the treatment, but the health-care practitioner has the possibility to select other deviations. Every change made by the health-care practitioner is identidied in the system to take it into account during further statistical analysis. When the deviations selected for the treatment are confirmed correctives exercises are automatically generated. A ten-week exercise schedule is generated which is, again, modifiable by the health-care practitioner if necessary. Exercises are selected compatible with a patient's activity level from low, to moderately to highly active. The health-care practitioner also has the opportunity to change exercise selection and/or schedule. The health-care practitioner can ask the system to increase or decrease the difficulty level of the program and generate a new schedule based on the request. The health-care practitioner can also remove or add exercises from the program because he or she thinks that a particular exercise can be harmful to the patient or to place emphasis on a particular deviation correction. Finally, health-care practitioner can reorganize the schedule in changing the order of exercises. Presented in Tables 2 and 3 are lists of deviations that are detectable by the current system, as well as the corrective actions by exercising and stretching to correct these deviations.

TABLE 2

Deviations - Exercises link

| Deviations | Actions | Exercises | | Levels |
|---|---|---|---|---|
| DIS001 | Translation of the head to the left | | | |
| | NHLF_L.S | NHFLRO19SR | Assisted neck extensor, lateral flexor and rotator stretch | 2,3 |
| | | NHL01 1SR | Neck lateral flexor stretch | * |
| | | NHLO17SR | Assisted neck lateral flexor stretch | 2,3 |
| | | NHLO24SR | Supine neck lateral flexor stretch | 1 |
| | | NHLRO14SL | Neck flexor, lateral flexor and rotator stretch | 1 |
| | | NHLRO155R | Neck extensor, lateral flexor and rotator stretch | 1 |
| | | NHLRO18SR | Assisted neck flexor, lateral flexor and rotator stretch | 2,3 |
| | | NHLR020SR | Assisted neck extensor, lateral flexor and rotator stretch | 2,3 |
| | | NHXL0055R | Assisted neck flexor and lateral flexor stretch | 2,3 |
| | | NHXLRO03SR | Neck flexor, rotator and lateral flexor stretch | 1 |
| | | NHXLRO07SR | Assisted neck flexor, lateral flexor and rotator stretch | 2,3 |
| | | NHXLRO08SR | Assisted neck flexor, lateral flexor and rotator stretch | 2,3 |
| | NHLF_R.C | NHLF010CR | Cervical strengthening | 1,2 |
| | | NHLF011CR | Supine cervical strengthening | 1 |
| | | NHLF012CR | Cervical strengthening with elastic resistance | 2,3 |
| DIS002 | Translation of the head to the right | | | |
| | NHLF_L.C | NHLF010CL | Cervical strengthening | 1,2 |
| | | NHLF01 1CL | Supine cervical strengthening | 1 |
| | | NHLF012CL | Cervical strengthening with elastic resistance | 2,3 |
| | NHLF_R.S | NHFLRO19SL | Assisted neck extensor, lateral flexor and rotator stretch | 2,3 |
| | | NHL01 1SL | Neck lateral flexor stretch | * |
| | | NHLO17SL | Assisted neck lateral flexor stretch | 2,3 |
| | | NHLO24SL | Supine neck lateral flexor stretch | 1 |
| | | NHLRO14SR | Neck flexor, lateral flexor and rotator stretch | 1 |
| | | NHLRO15SL | Neck extensor, lateral flexor and rotator stretch | 1 |
| | | NHLRO18SL | Assisted neck flexor, lateral flexor and rotator stretch | 2,3 |
| | | NHLR020SL | Assisted neck extensor, lateral flexor and rotator stretch | 2,3 |
| | | NHLRO21SL | Neck lateral flexor stretch | 2,3 |
| | | NHXL005SL | Assisted neck flexor and lateral flexor stretch | 2,3 |
| | | NHXLRO03SL | Neck flexor, rotator and lateral flexor stretch | 1 |
| | | NHXLRO07SL | Assisted neck flexor, lateral flexor and rotator stretch | 2,3 |
| | | NHXLRO08SL | Assisted neck flexor, lateral flexor and rotator stretch | 2,3 |
| DIS003 | Protrusion of the head | | | |
| | NHEX.S | NHF009SB | Neck extensor stretch | * |
| | NHFL.C | NHFL001CB | Cervical strengthening | 2 |
| | | NHFLO02CB | Cervical strengthening | * |
| | | NHFLO03CB | Supine cervical strengthening | 2 |
| | | NHFLO09CB | Cervical strengthening | 2 |
| | TRCE.C | TREX002CB | Prone trunk extension | 2,3 |
| | | TREX007CB | Arm and hip extension | 2,3 |
| | | TREX010CB | Prone lumbar extension with hands on the lower back | * |
| | | TREX011CB | Prone lumbar extension with hands behind your head | 2,3 |
| | | TREX012CB | Seated lumbar extension | 1 |
| DIS004 | Posterior deviation of the head | | | |
| | NHEX.S | NHF009SB | Neck extensor stretch | * |
| | NHFL.C | NHFL001CB | Cervical strengthening | 2 |
| | | NHFLO02CB | Cervical strengthening | * |
| | | NHFLO03CB | Supine cervical strengthening | 2 |
| | | NHFLO09CB | Cervical strengthening | 2 |
| | NHFL.S | NHEX001SB | Neck flexor stretch | 1 |
| | | NHXLRO04SB | Assisted neck flexor stretch | 2,3 |
| | TRCE.S | TREX004SB | Standing torso flexion with arms reaching down | * |
| | | TREX009SB | Supine back extensor stretch propped up on your elbows | 1 |
| DIS005 | Flexion of the head | | | |
| | NHEX.C | NHEX004CB | Cervical strengthening | 1 |
| | | NHEX005CB | Cervical strengthening | 1 |
| | | NHEX007CB | Cervical strengthening with elastic resistance | 2,3 |
| | | NHEX008CB | Prone cervical strengthening | 2 |
| | NHLF_L.S | NHFLRO19SR | Assisted neck extensor, lateral flexor and rotator stretch | 2,3 |
| | | NHL01 1SR | Neck lateral flexor stretch | * |
| | | NHLO17SR | Assisted neck lateral flexor stretch | 2,3 |
| | | NHLO24SR | Supine neck lateral flexor stretch | 1 |
| | | NHLRO14SL | Neck flexor, lateral flexor and rotator stretch | 1 |
| | | NHLRO15SR | Neck extensor, lateral flexor and rotator stretch | 1 |
| | | NHLR01 8SR | Assisted neck flexor, lateral flexor and rotator stretch | 2,3 |
| | | NHLR020SR | Assisted neck extensor, lateral flexor and rotator stretch | 2,3 |

TABLE 2-continued

Deviations - Exercises link

| Deviations | Actions | Exercises | | Levels |
|---|---|---|---|---|
| | | NHXL005SR | Assisted neck flexor and lateral flexor stretch | 2,3 |
| | | NHXLRO03SR | Neck flexor, rotator and lateral flexor stretch | 1 |
| | | NHXLRO07SR | Assisted neck flexor, lateral flexor and rotator stretch | 2,3 |
| | | NHXLRO08SR | Assisted neck flexor, lateral flexor and rotator stretch | 2,3 |
| | NHLF_R.S | NHFLRO19SL | Assisted neck extensor, lateral flexor and rotator stretch | 2,3 |
| | | NHL011SL | Neck lateral flexor stretch | * |
| | | NHLO17SL | Assisted neck lateral flexor stretch | 2,3 |
| | | NHLO24SL | Supine neck lateral flexor stretch | 1 |
| | | NHLRO14SR | Neck flexor, lateral flexor and rotator stretch | 1 |
| | | NHLRO15SL | Neck extensor, lateral flexor and rotator stretch | 1 |
| | | NHLRO18SL | Assisted neck flexor, lateral flexor and rotator stretch | 2,3 |
| | | NHLR020SL | Assisted neck extensor, lateral flexor and rotator stretch | 2,3 |
| | | NHLR021SL | Neck lateral flexor stretch | 2,3 |
| | | NHXL005SL | Assisted neck flexor and lateral flexor stretch | 2,3 |
| | | NHXLRO03SL | Neck flexor, rotator and lateral flexor stretch | 1 |
| | | NHXLRO07SL | Assisted neck flexor, lateral flexor and rotator stretch | 2,3 |
| | | NHXLRO08SL | Assisted neck flexor, lateral flexor and rotator stretch | 2,3 |
| | TRCE.C | TREX002CB | Prone trunk extension | 2,3 |
| | | TREX007CB | Arm and hip extension | 2,3 |
| | | TREX010CB | Prone lumbar extension with hands on the lower back | * |
| | | TREX011CB | Prone lumbar extension with hands behind your head | 2,3 |
| | | TREX012CB | Seated lumbar extension | 1 |
| DIS006 | Extension of the head | | | |
| | NHEX.S | NHF009SB | Neck extensor stretch | * |
| | NRFL.C | NHFL001CB | Cervical strengthening | 2 |
| | | NHFLO02CB | Cervical strengthening | * |
| | | NHFLO03CB | Supine cervical strengthening | 2 |
| | | NHFLO09CB | Cervical strengthening | 2 |
| | SCAD.S | SCAD001SB | Scapula adductor stretch with your hands behind your back | * |
| | | SCAD007SB | Scapula adductor stretch with your arms crossed | 1 |
| DIS009 | Lateral flexion of the head to the right | | | |
| | NHLF_L.C | NHLF010CL | Cervical strengthening | 1,2 |
| | | NHLF01 1CL | Supine cervical strengthening | 1 |
| | | NHLF012CL | Cervical strengthening with elastic resistance | 2,3 |
| | NHLF_R.S | NHFLRO19SL | Assisted neck extensor, lateral flexor and rotator stretch | 2,3 |
| | | NHL01 1SL | Neck lateral flexor stretch | * |
| | | NHLO17SL | Assisted neck lateral flexor stretch | 2,3 |
| | | NHLO24SL | Supine neck lateral flexor stretch | 1 |
| | | NHLRO14SR | Neck flexor, lateral flexor and rotator stretch | 1 |
| | | NHLRO15SL | Neck extensor, lateral flexor and rotator stretch | 1 |
| | | NHLRO18SL | Assisted neck flexor, lateral flexor and rotator stretch | 2,3 |
| | | NHLRO20SL | Assisted neck extensor, lateral flexor and rotator stretch | 2,3 |
| | | NHLRO21SL | Neck lateral flexor stretch | 2,3 |
| | | NHXL005SL | Assisted neck flexor and lateral flexor stretch | 2,3 |
| | | NHXLRO03SL | Neck flexor, rotator and lateral flexor stretch | 1 |
| | | NHXLRO07SL | Assisted neck flexor, lateral flexor and rotator stretch | 2,3 |
| | | NHXLR008SL | Assisted neck flexor, lateral flexor and rotator stretch | 2,3 |
| DIS010 | Lateral flexion of the head to the left | | | |
| | NHLF_L.S | NHFLRO19SR | Assisted neck extensor, lateral flexor and rotator stretch | 2,3 |
| | | NHL01 1SR | Neck lateral flexor stretch | * |
| | | NHLO17SR | Assisted neck lateral flexor stretch | 2,3 |
| | | NHLO24SR | Supine neck lateral flexor Stretch | 1 |
| | | NHLRO14SL | Neck flexor, lateral flexor and rotator stretch | 1 |
| | | NHLRO15SR | Neck extensor, lateral flexor and rotator stretch | 1 |
| | | NHLRO18SR | Assisted neck flexor, lateral flexor and rotator stretch | 2,3 |
| | | NHLR020SR | Assisted neck extensor, lateral flexor and rotator stretch | 2,3 |
| | | NHXL005SR | Assisted neck flexor and lateral flexor stretch | 2,3 |
| | | NHXLRO03SR | Neck flexor, rotator and lateral flexor stretch | 1 |
| | | NHXLRO07SR | Assisted neck flexor, lateral flexor and rotator stretch | 2,3 |
| | | NHXLRO08SR | Assisted neck flexor, lateral flexor and rotator stretch | 2,3 |
| | NHLF_R.C | NHLF010CR | Cervical strengthening | 1,2 |
| | | NHLF01 1CR | Supine cervical strengthening | 1 |
| | | NHLF012CR | Cervical strengthening with elastic resistance | 2,3 |
| DIS011 | Lateral translation of the trunk to the left | | | |
| | TRLF_L.C | TRFLO15CL | Isometric abdominal contraction with leg extension | 1 |
| | | TRLF001CL | Lateral flexion with a dumbbell | 2,3 |
| | | TRLF002CL | Lateral flexion with a dumbbell | 2,3 |
| | | TRLF003CL | Lateral flexion with a bar | 2,3 |

TABLE 2-continued

Deviations - Exercises link

| Deviations | Actions | Exercises | | Levels |
|---|---|---|---|---|
| | | TRLF004CL | Lateral flexion with a bar | 1 |
| | | TRLF005CL | Lateral flexion with elastic resistance | * |
| | | TRLF008CL | Lateral flexion on an incline bench with arms across the chest | 1,2 |
| | | TRLF009CL | Inclined lateral flexion with crossed arms, holding a weight | 3 |
| | TRLF_R.S | TRLF001SR | Standing lateral trunk flexor stretch | * |
| | TRTE_R.S | TREX004SB | Standing torso flexion with arms reaching down | * |
| | | TREX009SB | Supine back extensor stretch propped up on your elbows | 1 |
| DIS012 | Lateral translation of the trunk to the right | | | |
| | TRLF_L.S | TRLF001SL | Standing lateral trunk flexor stretch | * |
| | TRLF_R.C | TRFLO15CR | Isometric abdominal contraction with leg extension | 1 |
| | | TRLF001 CR | Lateral flexion with a dumbbell | 2,3 |
| | | TRLF002CR | Lateral flexion with a dumbbell | 2,3 |
| | | TRLF003CR | Lateral flexion with a bar | 2,3 |
| | | TRLF004CR | Lateral flexion with a bar | 1 |
| | | TRLF005CR | Lateral flexion with elastic resistance | * |
| | | TRLF008CR | Lateral flexion on an incline bench with arms across the chest | 1,2 |
| | | TRLF009CR | Inclined lateral flexion with crossed arms, holding a weight | 3 |
| | TRTE_L.S | TREX001SB | Cat stretch | * |
| | | TREX004SB | Standing torso flexion with arms reaching down | * |
| | | TREX009SB | Supine back extensor stretch propped up on your elbows | 1 |
| DIS013 | Anterior deviation | | | |
| | HIEX.S | HIEX012SB | Seated bilateral hamstring stretch | * |
| | | HIEX013SB | Seated bilateral hamstring stretch | 3 |
| | HIFL_L.S | HIFLO01SL | Standing hip flexor stretch | 2,3 |
| | | HIFLO02SL | Standing hip flexor stretch (partial) | 1 |
| | | HIFLO03SL | Standing hip flexor stretch with back leg elevated | 3 |
| | HIFL_R.S | HIFLO01SR | Standing hip flexor stretch | 2,3 |
| | | HIFLO02SR | Standing hip flexor stretch (partial) | 1 |
| | | HIFLO03SR | Standing hip flexor stretch with back leg elevated | 3 |
| | SCAD.C | SCAD001 CB | Shoulder shrugs with dumbbells held in semi-supination while inclined | 3 |
| | | SCAD002CB | Shoulder shrugs with dumbbells held in pronation while inclined | 3 |
| | | SCAD003CB | Seated scapular adduction | * |
| | SHAD.S | SHAD001 SB | Shoulder adductor stretch | * |
| | TRLE.C | TREX001 CB | Kneeling trunk extension | 2,3 |
| | | TREX002CB | Prone trunk extension | 2,3 |
| | | TREX007CB | Arm and hip extension | 2,3 |
| | | TREX010CB | Prone lumbar extension with hands on the lower back | * |
| | | TREX011CB | Prone lumbar extension with hands behind your head | 2,3 |
| | | TREX012CB | Seated lumbar extension | 1 |
| DIS014 | Posterior deviation | | | |
| | HIFL_L.S | HIFLO01SL | Standing hip flexor stretch | 2,3 |
| | | HIFLO02SL | Standing hip flexor stretch (partial) | 1 |
| | | HIFLO03SL | Standing hip flexor stretch with back leg elevated | 3 |
| | HIFL_R.S | HIFLO01SR | Standing hip flexor stretch | 2,3 |
| | | HIFLO02SR | Standing hip flexor stretch (partial) | 1 |
| | | HIFLO03SR | Standing hip flexor stretch with back leg elevated | 3 |
| | SCAD.S | SCAD001 SIB | Scapula adductor stretch with your hands behind your back | * |
| | | SCAD007SB | Scapula adductor stretch with your arms crossed | 1 |
| | TRFL.C | TRFL001CB | Abdominal crunch with feet elevated | 1 |
| | | TRFLO02CB | Abdominal crunch with feet on the ground | 1 |
| | | TRFLO03CB | Abdominal crunch with feet on the ground and lumbar support | 1 |
| | | TRFLO04CB | Abdominal crunch with arms crossed and feet elevated | 1,2 |
| | | TRFLO05CB | Abdominal crunch with hands behind the head and feet elevated | 2 |
| | | TRFLO06CB | Abdominal crunch with hands behind the head and feet on the floor | 2,3 |
| | | TRFLO07CB | Abdominal crunch with hands behind the head and feet on the floor | 2,3 |
| | | TRFLO08CB | Abdominal crunch with arms overhead and feet elevated | 2,3 |
| | | TRFLO09CB | Abdominal crunch with arms overhead and feet elevated | 2,3 |

TABLE 2-continued

Deviations - Exercises link

| Deviations | Actions | Exercises | | Levels |
|---|---|---|---|---|
| | | TRFLO12CB | Hip raises (lower abdominal crunch) | 3 |
| | | TRFLO13CB | Abdominal crunch with arms extended at the elbows, pointing forward | 2,3 |
| | | TRFLO14CB | Isometric abdominal contraction | 1 |
| | TRLE.S | TREX001 SB | Cat stretch | * |
| | | TREX002SB | Supine, knees to chest | 1,2 |
| | | TREX003SB | Standing torso flexion | 1,2 |
| | | TREX004SB | Standing torso flexion with arms reaching down | * |
| | | TREX006SB | Seated trunk flexion | 1 |
| | | TREX008SB | Seated full forward stretch | 1,2 |
| | TRTE.S | TREX001 SB | Cat stretch | * |
| | | TREX004SB | Standing torso flexion with arms reaching down | * |
| | | TREX009SB | Supine back extensor stretch propped up on your elbows | 1 |
| DIS015 | Trunk flexion | | | |
| | HIEX.S | HIEX012SB | Seated bilateral hamstring stretch | * |
| | | HIEX013SB | Seated bilateral hamstring stretch | 3 |
| | HIFL_L.S | HIFLO01SL | Standing hip flexor stretch | 2,3 |
| | | HIFLO02SL | Standing hip flexor stretch (partial) | 1 |
| | | HIFLO03SL | Standing hip flexor stretch with back leg elevated | 3 |
| | HIFL_R.S | HIFLO01SR | Standing hip flexor stretch | 2,3 |
| | | HIFLO02SR | Standing hip flexor stretch (partial) | 1 |
| | | HIFLO03SR | Standing hip flexor stretch with back leg elevated | 3 |
| | NHEX.S | NHF009SB | Neck extensor stretch | * |
| | SHAD.S | SHAD001SB | Shoulder adductor stretch | * |
| | TRLE.C | TREX001CB | Kneeling trunk extension | 2,3 |
| | | TREX002CB | Prone trunk extension | 2,3 |
| | | TREX007CB | Arm and hip extension | 2,3 |
| | | TREX010CB | Prone lumbar extension with hands on the lower back | * |
| | | TREX011CB | Prone lumbar extension with hands behind your head | 2,3 |
| | | TREX012CB | Seated lumbar extension | 1 |
| | TRTE.C | TREX001 CB | Kneeling trunk extension | 2,3 |
| | | TREX002CB | Prone trunk extension | 2,3 |
| | | TREX007CB | Arm and hip extension | 2,3 |
| | | TREX010CB | Prone lumbar extension with hands on the lower back | * |
| | | TREX011CB | Prone lumbar extension with hands behind your head | 2,3 |
| | | TREX012CB | Seated lumbar extension | 1 |
| DIS016 | Trunk extension | | | |
| | NHEX_L.S | NHF009SB | Neck extensor stretch | * |
| | | NHFR010SL | Assisted neck extensor, lateral flexor and rotator stretch | * |
| | NHEX_R.S | NHF009SB | Neck extensor stretch | * |
| | | NHFRO10SR | Assisted neck extensor, lateral flexor and rotator stretch | * |
| | SCAB.C | SCAB001CB | Abdominal crunch with hands behind the head and feet on the floor | * |
| | SCAD.S | SCAD001SB | Scapula adductor stretch with your hands behind your back | * |
| | | SCAD007SB | Scapula adductor stretch with your arms crossed | 1 |
| | TRLF_L.S | TRLF001SL | Standing lateral trunk flexor stretch | * |
| | TRLF_R.S | TRLF001 SR | Standing lateral trunk flexor stretch | * |
| | TRTE.S | TREX001SB | Cat stretch | * |
| | | TREX004SB | Standing torso flexion with arms reaching down | * |
| | | TREX009SB | Supine back extensor stretch propped up on your elbows | 1 |
| DIS019 | Lateral flexion of the trunk to the right | | | |
| | TRLF_L.C | TRFLO15CL | Isometric abdominal contraction with leg extension | 1 |
| | | TRLF001CL | Lateral flexion with a dumbbell | 2,3 |
| | | TRLF002CL | Lateral flexion with a dumbbell | 2,3 |
| | | TRLF003CL | Lateral flexion with a bar | 2,3 |
| | | TRLF004CL | Lateral flexion with a bar | 1 |
| | | TRLF005CL | Lateral flexion with elastic resistance | * |
| | | TRLF008CL | Lateral flexion on an incline bench with arms across the chest | 1,2 |
| | | TRLF009CL | Inclined lateral flexion with crossed arms, holding a weight | 3 |
| | TRLF_R.S | TRLF001 SR | Standing lateral trunk flexor stretch | * |
| DIS020 | Lateral flexion of the trunk to the left | | | |
| | TRLF_L.S | TRLF001SL | Standing lateral trunk flexor stretch | * |
| | TRLF_R.C | TRFLO15 CR | Isometric abdominal contraction with leg extension | 1 |
| | | TRLF001 CR | Lateral flexion with a dumbbell | 2,3 |
| | | TRLF002CR | Lateral flexion with a dumbbell | 2,3 |
| | | TRLF003CR | Lateral flexion with a bar | 2,3 |
| | | TRLF004CR | Lateral flexion with a bar | 1 |
| | | TRLF005CR | Lateral flexion with elastic resistance | |

TABLE 2-continued

Deviations - Exercises link

| Deviations | Actions | Exercises | | Levels |
|---|---|---|---|---|
| | | TRLF008CR | Lateral flexion on an incline bench with arms across the chest | 1,2 |
| | | TRLF009CR | Inclined lateral flexion with crossed arms, holding a weight | 3 |
| DIS021 | Translation of the hip to the left | | | |
| | HIAB_L.C | HIAB001CL | Side lying hip abductor contraction | 1 |
| | | HIABO02CL | Side lying hip abductor contraction | 1 |
| | | HIABO03CB | Bilateral hip abductor contraction | 2,3 |
| | | HIABO04CL | Unilateral hip abduction exercise | 1,2 |
| | | HIABO05CL | Supine, anterior, unilateral hip abduction exercise with an elastic | 2,3 |
| | | HIABO06CL | Side lying hip abductor contraction with dumbbells | 2,3 |
| | | HIABO07CL | Side lying hip abductor contraction with elastic resistance | 2,3 |
| | | HIABO08CL | Side lying hip abductor contraction with added weight | * |
| | | HIAB011 CL | Standing unilateral hip abduction exercise | 2,3 |
| | | HIABO12CL | Standing, anterior, unilateral hip abduction exercise | 2,3 |
| | | HIABO13CL | Standing, posterior, unilateral hip abduction exercise | 2,3 |
| | HIAB_R.S | HIABO01SR | Side lying hip abductor stretch | 1,2,3 |
| | | HIABO05SR | Standing hip abductor stretch | 2,3 |
| | | HIABO06SR | Standing hip abductor stretch with lateral flexion | 2,3 |
| | | HIABO07SR | Standing hip abductor stretch with lateral flexion | * |
| | HIAD_L.S | HIAD005SL | Standing hip adductor stretch | * |
| | | HIAD008SL | Kneeling hip adductor stretch | 3 |
| | HIAD_R.C | HIAD001CR | Side tying isometric hip adduction | * |
| | | HIAD002CR | Supine hip adduction with elastic resistance | 2,3 |
| | | HIAD003CR | Side lying hip adduction | 2,3 |
| | | HIAD006CS | Supine hip adduction with a ball between the knees | 1,2 |
| | | HIAD010CB | Supine hip adduction with a ball between the knees | 1,2 |
| | | HIAD011CR | Side lying hip adduction with a ball placed between your feet | 1,2 |
| | | HIAD012CR | Side lying hip adduction with a ball between the knees and thighs | 1,2 |
| DIS022 | Translation of the hip to the right | | | |
| | HIAB_L.S | HIABO01SL | Side lying hip abductor stretch | 1,2,3 |
| | | HIABO05SL | Standing hip abductor stretch | 2,3 |
| | | HIABO06SL | Standing hip abductor stretch with lateral flexion | 2,3 |
| | | HIABO07SL | Standing hip abductor stretch with lateral flexion | * |
| | HIAB_R.C | HIABO01CR | Side lying hip abductor contraction | 1 |
| | | HIABO02CR | Side lying hip abductor contraction | * |
| | | HIABO03CB | Bilateral hip abductor contraction | 2,3 |
| | | HIABO04CR | Unilateral hip abductor exercise | 1,2 |
| | | HIABO05CR | Supine, anterior, unilateral hip abduction exercise with an elastic | 2,3 |
| | | HIABO06CR | Side lying hip abductor contraction with dumbbells | 2,3 |
| | | HIABO07CR | Side lying hip abductor contraction with elastic resistance | 2,3 |
| | | HIABO08CR | Side lying hip abductor contraction with added weight | 3 |
| | | HIAB011 CR | Standing unilateral hip abduction exercise | 2,3 |
| | | HIABO12CR | Standing, anterior, unilateral hip abduction exercise | 2,3 |
| | | HIABO13CR | Standing, posterior, unilateral hip abduction exercise | 2,3 |
| | HIAD_L.C | HIAD001CL | Side lying isometric hip adduction | 1 |
| | | HIAD002CL | Supine hip adduction with elastic resistance | 2,3 |
| | | HIAD003CL | Side lying hip adduction | 2,3 |
| | | HIAD006CB | Supine hip adduction with a ball between the knees | 1,2 |
| | | HIAD010CB | Supine hip adduction with a ball between the knees | 1,2 |
| | | HIAD011CL | Side lying hip adduction with a ball placed between your feet | 1,2 |
| | | HIAD012CL | Side lying hip adduction with a ball between the knees and thighs | 1,2 |
| | HIAD_R.S | HIAD005SR | Standing hip adductor stretch | * |
| | | HDAD008SR | Kneeling hip adductor stretch | 3 |
| DIS023 | Anterior translation of the hip | | | |
| | HIEX.C | HIEX001CB | Supine pelvic tilt | * |
| | HIFL_L.S | HIFLO01SL | Standing hip flexor stretch | 2,3 |
| | | HIFLO02SL | Standing hip flexor stretch (partial) | 1 |
| | | HIFLO03SL | Standing hip flexor stretch with back leg elevated | 3 |
| | HIFL_R.S | HIFLO01SR | Standing hip flexor stretch | 2,3 |
| | | HIFLO02SR | Standing hip flexor stretch (partial) | 1 |
| | | HIFLO03SR | Standing hip flexor stretch with back leg elevated | 3 |
| DIS024 | Posterior translation of the hip | | | |
| | HIEX_L.S | HIEX001SL | Standing hamstring stretch | * |
| | | HIEX002SL | Supine hamstring stretch | 2,3 |
| | | HIEX003SL | Supine hamstring stretch | 1 |
| | | HIEX004SL | Supine hamstring stretch | 1 |

TABLE 2-continued

Deviations - Exercises link

| Deviations | Actions | Exercises | | Levels |
|---|---|---|---|---|
| | | HIEX007SL | Supine hamstring stretch | 1 |
| | | HIEX008SL | Supine hamstring stretch | 2,3 |
| | | HIEX011SL | Seated hamstring stretch | 2,3 |
| | | HIEX012SB | Seated bilateral hamstring stretch | * |
| | | HIEX013SB | Seated bilateral hamstring stretch | 3 |
| | | HIEX014SL | Standing hamstring stretch | 2,3 |
| | HIEX_R.S | HIEX001SR | Standing hamstring stretch | * |
| | | HIEX002SR | Supine hamstring stretch | 2,3 |
| | | HIEX003SR | Supine hamstring stretch | 1 |
| | | HIEX004SR | Supine hamstring stretch | 1 |
| | | HIEX007SR | Supine hamstring stretch | 1 |
| | | HIEX008SR | Supine hamstring stretch | 2,3 |
| | | HIEX01 1SR | Seated hamstring stretch | 2,3 |
| | | HIEX012SB | Seated bilateral hamstring stretch | * |
| | | HIEX013SB | Seated bilateral hamstring stretch | 3 |
| | | HIEX014SR | Standing hamstring stretch | 2,3 |
| | HIFL_L.C | HIFL001CB | Squat | * |
| | | HIFLO02CB | Unilateral squat | * |
| | | TRFLO10CL | Abdominal crunch with unilateral hip flexion | 2,3 |
| | | TRFLO11CL | Abdominal crunch with arms overhead and unilateral hip flexion | 2,3 |
| | | TRFLO12CB | Hip raises (lower abdominal crunch) | 3 |
| | HIFL_R.C | HIFL001CB | Squat | * |
| | | HIFLO02CB | Unilateral squat | * |
| | | TRFL010CR | Abdominal crunch with unilateral hip flexion | 2,3 |
| | | TRRLO11CR | Abdominal crunch with arms overhead and feet elevated | 2,3 |
| | | TRFLO12CB | Hip raises (lower abdominal crunch) | 3 |
| DIS025 | Anterior pelvic tilt | | | |
| | HIEX.C | HIEX001CB | Supine pelvic tilt | * |
| | HIEX_L.S | HIEX001SL | Standing hamstring stretch | * |
| | | HIEX002SL | Supine hamstring stretch | 2,3 |
| | | HIEX003SL | Supine hamstring stretch | 1 |
| | | HIEX004SL | Supine hamstring stretch | 1 |
| | | HIEX007SL | Supine hamstring stretch | 1 |
| | | HIEX008SL | Supine hamstring stretch | 2,3 |
| | | HIEX01 1SL | Seated hamstring stretch | 2,3 |
| | | HIEX012SB | Seated bilateral hamstring stretch | * |
| | | HIEX013SB | Seated bilateral hamstring stretch | 3 |
| | | HIEX014SL | Standing hamstring stretch | 2,3 |
| | HIEX_R.S | HIEX001SR | Standing hamstring stretch | * |
| | | HIEX002SR | Supine hamstring stretch | 2,3 |
| | | HIEX003SR | Supine hamstring stretch | 1 |
| | | HIEX004SR | Supine hamstring stretch | 1 |
| | | HIEX007SR | Supine hamstring stretch | 1 |
| | | HIEX008SR | Supine hamstring stretch | 2,3 |
| | | HIEX01 1SR | Seated hamstring stretch | 2,3 |
| | | HIEX012SB | Seated bilateral hamstring stretch | * |
| | | HIEX013SB | Seated bilateral hamstring stretch | 3 |
| | | HIEX014SR | Standing hamstring stretch | 2,3 |
| | HIFL_L.S | HIFLO01SL | Standing hip flexor stretch | 2,3 |
| | | HIFLO02SL | Standing hip flexor stretch (partial) | 1 |
| | | HIFLO03SL | Standing hip flexor stretch with back leg elevated | 3 |
| | HIFL_R.S | HIFLO01SR | Standing hip flexor stretch | 2,3 |
| | | HIFLO02SR | Standing hip flexor stretch (partial) | 1 |
| | | HIFLO03SR | Standing hip flexor stretch with back leg elevated | 3 |
| | TRFL.C | TRFL001CB | Abdominal crunch with feet elevated | 1 |
| | | TRFLO02CB | Abdominal crunch with feet on the ground | 1 |
| | | TRFLO03CB | Abdominal crunch with feet on the ground and lumbar support | 1 |
| | | TRFLO04CB | Abdominal crunch with arms crossed and feet elevated | 1,2 |
| | | TRFLO05CB | Abdominal crunch with hands behind the head and feet elevated | 2 |
| | | TRFLO06CB | Abdominal crunch with hands behind the head and feet on the floor | 2,3 |
| | | TRFLO07CB | Abdominal crunch with hands behind the head and feet on the floor | 2,3 |
| | | TRFLO08CB | Abdominal crunch with arms overhead and feet elevated | 2,3 |
| | | TRFLO09CB | Abdominal crunch with arms overhead and feet elevated | 2,3 |

TABLE 2-continued

Deviations - Exercises link

| Deviations | Actions | Exercises | | Levels |
|---|---|---|---|---|
| | | TRFLO12CB | Hip raises (lower abdominal crunch) | 3 |
| | | TRFLO13CB | Abdominal crunch with arms extended at the elbows, pointing forward | 2,3 |
| | | TRFLO14CB | Isometric abdominal contraction | 1 |
| | TRLE.S | TRFX001 SB | Cat stretch | * |
| | | TREX002SB | Supine, knees to chest | 1,2 |
| | | TREX003SB | Standing torso flexion | 1,2 |
| | | TREX004SB | Standing torso flexion with arms reaching down | * |
| | | TREX006SB | Seated trunk flexion | 1 |
| | | TREX008SB | Seated full forward stretch | 1,2 |
| DIS026 | Posterior pelvic tilt | | | |
| | HIEX_L.S | HIEX001SL | Standing hamstring stretch | * |
| | | HIEX002SL | Supine hamstring stretch | 2,3 |
| | | HIEX003SL | Supine hamstring stretch | 1 |
| | | HIEX004SL | Supine hamstring stretch | 1 |
| | | HIEX007SL | Supine hamstring stretch | 1 |
| | | HIEX008SL | Supine hamstring stretch | 2,3 |
| | | HIEX01 1SL | Seated hamstring stretch | 2,3 |
| | | HIEX012SB | Seated bilateral hamstring stretch | * |
| | | HIEX013SB | Seated bilateral hamstring stretch | 3 |
| | | HIEX014SL | Standing hamstring stretch | 2,3 |
| | HIEX_R.S | HIEX001SR | Standing hamstring stretch | * |
| | | HIEX002SR | Supine hamstring stretch | 2,3 |
| | | HIEX003SR | Supine hamstring stretch | 1 |
| | | HIEX004SR | Supine hamstring stretch | 1 |
| | | HIEX007SR | Supine hamstring stretch | 1 |
| | | HIEX008SR | Supine hamstring stretch | 2,3 |
| | | HIEX01 1SR | Seated hamstring stretch | 2,3 |
| | | HIEX012SB | Seated bilateral hamstring stretch | * |
| | | HIEX013SB | Seated bilateral hamstring stretch | 3 |
| | | HIEX014SR | Standing hamstring stretch | 2,3 |
| | HIFL_L.C | HIFL001CB | Squat | * |
| | | HIFLO02CB | Unilateral squat | * |
| | | TRFLO10CL | Abdominal crunch with unilateral hip flexion | 2,3 |
| | | TRFLO11CL | Abdominal crunch with arms overhead and unilateral hip flexion | 2,3 |
| | | TRFLO12CB | Hip raises (lower abdominal crunch) | 3 |
| | HIFL_R.C | HIFL001CB | Squat | * |
| | | HIFLO02CB | Unilateral squat | * |
| | | TRFLO10CR | Abdominal crunch with unilateral hip flexion | 2,3 |
| | | TRFLO11CR | Abdominal crunch with arms overhead and feet elevated | 2,3 |
| | | TRFLO12CB | Hip raises (lower abdominal crunch) | 3 |
| | TRFL.S | TRFL001SB | Cobra | * |
| | TRLE.C | TREX001CB | Kneeling trunk extension | 2,3 |
| | | TREX002CB | Prone trunk extension | 2,3 |
| | | TREX007CB | Arm and hip extension | 2,3 |
| | | TREX010CB | Prone lumbar extension with hands on the lower back | * |
| | | TREX011CB | Prone lumbar extension with hands behind your head | 2,3 |
| | | TREX012CB | Seated lumbar extension | 1 |
| DIS029 | Lateral elevation of the hip to the left | | | |
| | TRFL.S | TRFL001 SIB | Cobra | * |
| | TRLE.C | TREX001CB | Kneeling trunk extension | 2,3 |
| | | TREX002CB | Prone trunk extension | 2,3 |
| | | TREX007CB | Arm and hip extension | 2,3 |
| | | TREX010CB | Prone lumbar extension with hands on the lower back | * |
| | | TREX011CB | Prone lumbar extension with hands behind your head | 2,3 |
| | | TREX012CB | Seated lumbar extension | 1 |
| | TRLF_L.S | TRLF001 SL | Standing lateral trunk flexor stretch | * |
| | TRLF_R.C | TRFLO15CR | Isometric abdominal contraction with leg extension | 1 |
| | | TRLF001CR | Lateral flexion with a dumbbell | 2,3 |
| | | TRLF002CR | Lateral flexion with a dumbbell | 2,3 |
| | | TRLF003CR | Lateral flexion with a bar | 2,3 |
| | | TRLF004CR | Lateral flexion with a bar | 1 |
| | | TRLF005CR | Lateral flexion with elastic resistance | * |
| | | TRLF008CR | Lateral flexion on an incline bench with arms across the chest | 1,2 |
| | | TRLF009CR | Inclined lateral flexion with crossed arms, holding a weight | 3 |
| | TRTE.C | TREX001CB | Kneeling trunk extension | 2,3 |
| | | TREX002CB | Prone trunk extension | 2,3 |
| | | TREX007CB | Arm and hip extension | 2,3 |
| | | TREX010CB | Prone lumbar extension with hands on the lower back | * |
| | | TREX011CB | Prone lumbar extension with hands behind your head | 2,3 |
| | | TREX012CB | Seated lumbar extension | 1 |

TABLE 2-continued

Deviations - Exercises link

| Deviations | Actions | Exercises | | Levels |
|---|---|---|---|---|
| DIS030 | Lateral elevation of the hip to the right | | | |
| | TRFL.C | TRFL001CB | Abdominal crunch with feet elevated | 1 |
| | | TRFLO02CB | Abdominal crunch with feet on the ground | 1 |
| | | TRFLO03CB | Abdominal crunch with feet on the ground and lumbar support | 1 |
| | | TRFLO04CB | Abdominal crunch with arms crossed and feet elevated | 1,2 |
| | | TRFLO05CB | Abdominal crunch with hands behind the head and feet elevated | 2 |
| | | TRFLO06CB | Abdominal crunch with hands behind the head and feet on the floor | 2,3 |
| | | TRFLO07CB | Abdominal crunch with hands behind the head and feet on the floor | 2,3 |
| | | TRFL008CB | Abdominal crunch with arms overhead and feet elevated | 2,3 |
| | | TRFLO09CB | Abdominal crunch with arms overhead and feet elevated | 2,3 |
| | | TRFLO12CB | Hip raises (lower abdominal crunch) | 3 |
| | | TRFLO13CB | Abdominal crunch with arms extended at the elbows, pointing forward | 2,3 |
| | | TRFLO14CB | Isometric abdominal contraction | 1 |
| | TRLE.S | TREX001 SB | Cat stretch | * |
| | | TREX002SB | Supine, knees to chest | 1,2 |
| | | TREX003SB | Standing torso flexion | 1,2 |
| | | TREX004SB | Standing torso flexion with arms reaching down | * |
| | | TREX006SB | Seated trunk flexion | 1 |
| | | TREX008SB | Seated full forward stretch | 1,2 |
| | TRLF$_L$_L.C | | | |
| | | TRFLO15CL | Isometric abdominal contraction with leg extension | 1 |
| | | TRLF001CL | Lateral flexion with a dumbbell | 2,3 |
| | | TRLF002CL | Lateral flexion with a dumbbell | 2,3 |
| | | TRLF003CL | Lateral flexion with a bar | 2,3 |
| | | TRLF004CL | Lateral flexion with a bar | 1 |
| | | TRLF005CL | Lateral flexion with elastic resistance | |
| | | TRLF008CL | Lateral flexion on an incline bench with arms across the chest | 1,2 |
| | | TRLF009CL | Inclined lateral flexion with crossed arms, holding a weight | 3 |
| | TRLF_R.S | TRLF001SR | Standing lateral trunk flexor stretch | * |
| | TRTE.S | TREX001 SB | Cat stretch | * |
| | | TREX004SB | Standing torso flexion with arms reaching down | * |
| | | TREX009SB | Supine back extensor stretch propped up on your elbows | 1 |
| DIS031 | Plantar flexion of the right foot | | | |
| | ANDF_R.C | ANDF001 CB | Bilateral toe raises | 2,3 |
| | | ANDF002CR | Ankle dorsiflexion with elastic resistance | 1,2 |
| | ANPF R. S | AN PF001 SR | Supine plantar flexor stretch | |
| | | ANPF002SR | Supine plantar flexor stretch with a towel | 2 |
| | | ANPF003SR | Standing plantar flexor stretch | 1,2 |
| | | ANPF004SB | Standing bilateral plantar flexor stretch | 2 |
| DIS032 | Dorsiflexion of the right foot | | | |
| | ANDF R. S | ANDF001 SR | Seated ankle dorsiflexor stretch | |
| | ANPF R. C | ANPF001 CR | Standing plantar flexor isometric contraction | 3 |
| | | ANPF002CB | Bilateral isometric plantar flexor contraction with a ball | 1 |
| | | ANPF004CB | Standing bilateral plantar flexor strengthening | 1,2 |
| | | ANPF005CR | Standing plantar flexor strengthening | 3 |
| | | ANPF006CR | Seated plantar flexor strengthening with elastic resistance | 1,2 |
| DIS033 | Internal rotation of the right foot | | | |
| | ANEV R. C | ANEVC001 CR | Seated ankle eversion with elastic resistance | |
| | HIER R. C | HIER001 CR | Side lying hip abductor f external rotator exercise | ' |
| | | HIER002CB | Seated bilateral hip abductor/external rotator exercise | ' |
| | | HIER003CR | Side lying hip abductor/external rotator contractions with a dumbbell | |
| | HIEX L. S | HIEX001 SL | Standing hamstring stretch | ' |
| | | HIEX002SL | Supine hamstring stretch | 2,3 |
| | | HIEX003SL | Supine hamstring stretch | 1 |
| | | HIEX004SL | Supine hamstring stretch | 1 |
| | | HIEX007SL | Supine hamstring stretch | 9 |
| | | HIEX008SL | Supine hamstring stretch | 2,3 |
| | | HIEX011SL | Seated hamstring stretch | 2,3 |
| | | HIEX012SB | Seated bilateral hamstring stretch (legs apart) | |

TABLE 2-continued

Deviations - Exercises link

| Deviations | Actions | Exercises | | Levels |
|---|---|---|---|---|
| | | HIEX013SB | Seated bilateral hamstring stretch (legs together) | 3 |
| | | HIEX014SL | Standing hamstring stretch | 2,3 |
| | | HIEX015SL | Supine hamstring stretch | |
| | HIEX R. C | HIEX001 CB | Supine pelvic flit | |
| | | HIEX003CR | Supine pelvic tilt | 2,3 |
| | | HIEX004CR | Supine pelvic tilt with one leg extended at the knee | 3 |
| | | HIEX005CR | Kneeling hip extensor exercise (leg flexed at the knee) | 2 |
| | | HIEX006CR | Kneeling hip extensor exercise (leg extended) | 2,3 |
| | HIFL L.S | HIFL001 SL | Standing hip flexor stretch | 2,3 |
| | | HIFLO02SL | Standing hip flexor stretch (partial) | 1 |
| | | HIFLO03SL | Standing hip flexor stretch with back leg elevated | 3 |
| | HIFL R. C | HIFL001CB | Squat | ' |
| | | TRFLO10CR | Abdominal crunch with unilateral hip flexion | 2,3 |
| | | I CR | Abdominal crunch with arms overhead and unilateral hip flexion | 2,3 |
| | | TRFLO12CS | Hip raises (lower abdominal contraction) | 3 |
| DIS034 | External rotation of the right foot | | | |
| | AKIN R. C | ANINCO01 CR | Seated ankle inversion with elastic resistance | |
| | HIER R.S | HIER002SR | Supine hip external rotator stretch | 3 |
| | | HIER003SR | Supine hip external rotator stretch | 1 |
| | | HIER004SR | Supine assisted hip external rotator stretch | 1,2 |
| | | HIER005SR | Supine assisted hip external rotator stretch | 3 |
| | | HIER006SR | Seated assisted hip external rotator stretch | 1 |
| | | HIER009SR | Supine assisted hip external rotator stretch | 2,3 |
| | | HIER012SR | Prone hip external rotator stretch | ' |
| | HIE X R. S | HIEX001SR | Standing hamstring stretch | |
| | | HIEX002SR | Supine hamstring stretch | 2,3 |
| | | HIEX003SR | Supine hamstring stretch | 1 |
| | | HIEX004SR | Supine hamstring stretch | 1 |
| | | HIEX007SR | Supine hamstring stretch | 1 |
| | | HIEX008SR | Supine hamstring stretch | 2,3 |
| | | HIEX011SR | Seated hamstring stretch | 2,3 |
| | | HIEX012SB | Seated bilateral hamstring stretch (legs apart) | |
| | | HIEX013SB | Seated bilateral hamstring stretch (legs together) | 3 |
| | | HIEX014SR | Standing hamstring stretch | 2,3 |
| | | HIEX015SR | Supine hamstring stretch | ' |
| | HIFL R.S | HIFIL001SR | Standing hip flexor stretch | 2,3 |
| | | HIFLO02SR | Standing hip flexor stretch (partial) | 1 |
| | | HIFLO03SR | Standing hip flexor stretch with back leg elevated | 3 |
| | HIIR R. C | HIIRO01CR | Side lying isometric hip adduction and internal rotation | |
| | | HIIR002CB | Supine knee-to-knee adduction and internal rotation | |
| | | HIIR003CB | Supine hip adduction and internal rotation with a ball | TRFLDI |
| DIS037 | Genu valgum right | | | |
| | HLAB R. S | HIAB001 SR | Side lying hip abductor stretch | 1,2,3 |
| | | HIABO05SR | Standing hip abductor stretch | 2,3 |
| | | HIABO06SR | Standing hip abductor stretch with lateral flexion | 2,3 |
| | | HIABO07SR | Standing hip abductor stretch witn lateral flexion | |
| | HLAD R. C | HIAD001 CR | Side lying isometric hip adduction | ' |
| | | HIAD002CR | Supine hip adduction with elastic resistance | 2,3 |
| | | HIAD003CR | Side lying hip adduction with elastic resistance | 2,3 |
| | | HIAD006CB | Supine hip adduction with a ball between the knees | 1,2 |
| | | HIAD010CB | Supine hip adduction with a ball between the knees | 1,2 |
| | | HIAD011CR | Side lying hip adduction with a ball placed between your ankles | 1,2 |
| | | HIAD012OR | Side lying hip adduction with a ball between the knees and thighs | 1,2 |
| DIS038 | Genu valgum left | | | |
| | HIAB L. S | HIAB001 SL | Side lying hip abductor stretch | 1,2,3 |
| | | HIABO05SL | Standing hip abductor stretch | 2,3 |
| | | HIABO06SL | Standing hip abductor stretch with lateral flexion | 2,3 |
| | | HIABO07SL | Standing hip abductor stretch with lateral flexion | ' |
| | HIAD L. C | HIAD001CL | Side lying isometric hip adduction | 1 |
| | | HIAD002CL | Supine hip adduction with elastic resistance | 2,3 |
| | | HIAD003CL | Side lying hip adduction with elastic resistance | 2,3 |
| | | HIAD006CB | Supine hip adduction with a ball between the knees | 1,2 |
| | | HIAD010CB | Supine hip adduction with a ball between the knees | 1,2 |
| | | HIAD011CL | Side lying hip adduction with a ball placed between your ankles | 1,2 |
| | | HIAD012CL | Side lying hip adduction with a ball between the knees and thighs | 1,2 |
| DIS039 | Genu varum right | | | |
| | HIAB R. C | HIAB001 CR | Side lying hip abductor contraction | 1 |
| | | HIAB002CR | Side lying hip abductor contraction | ' |
| | | HIABO03CB | Seated bilateral hip abduction with elastic resistance | 2,3 |
| | | HIABO04CR | Side lying hip abduction exercise | 1,2 |

TABLE 2-continued

Deviations - Exercises link

| Deviations | Actions | Exercises | | Levels |
|---|---|---|---|---|
| | | HIABO05CR | Supine hip abduction exercise with elastic resistance | 2,3 |
| | | HIABO06CR | Side lying hip abductor exercise with dumbbells | 2,3 |
| | | HIABO07CR | Side lying hip abductor contraction with elastic resistance | 2,3 |
| | | HIABO08CR | Side lying hip abductor contraction with added weight | 3 |
| | | HIABO11CR | Standing hip abduction exercise with elastic resistance | 2,3 |
| | | HIABO12CR | Standing hip abduction exercise with elastic resistance | 2,3 |
| | | HIAB013CR | Standing hip abduction exercise with elastic resistance | 2,3 |
| | HIAD R.S | HIAD005SR | Standing hip adductor stretch | |
| | | HIAD008SR | Kneeling hip adductor stretch | 3 |
| DIS040 | Genu varum left | | | |
| | HIAB L. C | HIA8001CL | Side lying hip abductor contraction | 1 |
| | | HIABO02CL | Side lying hip abductor contraction | 1 |
| | | HIABO03CB | Seated bilateral hip abduction with elastic resistance | 2,3 |
| | | HIABO04CL | Side lying hip abduction exercise | 1,2 |
| | | HIABO05CL | Supine hip abduction exercise with elastic resistance | 2,3 |
| | | HIABO06CL | Side lying hip abductor exercise with dumbbells | 2,3 |
| | | HIABO07CL | Side lying hip abductor contraction with elastic resistance | 2,3 |
| | | HIAB008CL | Side lying hip abductor contraction with added weight | |
| | | HIABO11CL | Standing tip abduction exercise with elastic resistance | 2,3 |
| | | HIABO12CL | Standing hip abduction exercise with elastic resistance | 2,3 |
| | | HIABO13CL | Standing hip abduction exercise with elastic resistance | 2,3 |
| | HIAD L.S | HIAD005SL | Standing hip adductor stretch | ' |
| | | HIAD008SL | Kneeling hip adductor stretch | 3 |
| DIS041 | Anterior deviation of the shoulders | | | |
| | SCAR C | SCAD001 CB | Shoulder shrugs with dumbbells held in semi-supination on an incline | 3 |
| | | SCAD002CB | Shoulder shrugs with dumbbells held In pronation on an incline bench | 3 |
| | | SCAD003CS | Seated scapula adductor exercise | ' |
| | SHFL.S | SHFLO05SB | Assisted shoulder flexor stretch | |
| | SHIR. S | SHIR006SR | Bent-over shoulder stretch | |
| DIS042 | Posterior deviation of the shoulders | | | |
| | SCAB. C | SCAB001CB | Abdominal crunch with hands behind your head and feet on the floor | |
| | SCAD. S | SCAD001 SB | Scapula adductor stretch with both hands behind your back | |
| | | SCAD007SB | Scapula adductor stretch with your arms crossed | 1 |
| | SHFL. C | SHFL001 CB | Standing bilateral shoulder flexor exercise with a ball | 1,2 |
| | | SHFLO02CB | Standing bilateral shoulder flexor exercise with a ball | 1,2 |
| | | SHFLO03CB | Shoulder flexor exercise with elastic resistance | 1,2 |
| | | SHFLO05CB | Forward shoulder flexion with 3 elastics | 2,3 |
| | | SHFLO06CB | Standing shoulder forward flexion with dumbbells | 3 |
| | | SHFLO07CB | Standing shoulder forward flexion and rotation with dumbbells | 3 |
| | SHIR. C | SHABO03CB | Bilateral shoulder abduction with dumbbells (palms backward) | 3 |
| | | SHIR002CB | Prone shoulder internal rotator exercise with bar and elastics | |
| DIS043 | External rotation of the left foot | | | |
| | ANIN L. C | ANINCO01CL | Seated ankle inversion with elastic resistance | |
| | HIER L. S | HIER002SL | Supine hip external rotator stretch | 3 |
| | | HIER003SL | Supine hip external rotator stretch | 1 |
| | | HIER004SL | Supine assisted hip external rotator stretch | 1,2 |
| | | HIER005SL | Supine assisted hip external rotator stretch | 3 |
| | | HIER006SL | Seated assisted hip external rotator stretch | 1 |
| | | HIER009SL | Supine assisted hip external rotator stretch | 2,3 |
| | | HIER012SL | Prone hip external rotator stretch | |
| | HIEX L. S | HIEX001SL | Standing hamstring stretch | |
| | | HIEX002SL | Supine hamstring stretch | 2,3 |
| | | HIEX003SL | Supine hamstring stretch | 1 |
| | | HIEX004SL | Supine hamstring stretch | 1 |
| | | HIEX007SL | Supine hamstring stretch | 1 |
| | | HIEX008SL | Supine hamstring stretch | 2,3 |
| | | HIEX011SL | Seated hamstring stretch | 2,3 |
| | | HiEX012SB | Seated bilateral hamstring stretch (legs apart) | |

TABLE 2-continued

Deviations - Exercises link

| Deviations | Actions | Exercises | | Levels |
|---|---|---|---|---|
| | | HIEX013SB | Seated bilateral hamstring stretch (legs together) | 3 |
| | | HIEX014SL | Standing hamstring stretch | 2,3 |
| | | HIEX015SL | Supine hamstring stretch | |
| | HIFL L. S | HIFLO01SL | Standing hip flexor stretch | 2,3 |
| | | HIFLO02SL | Standing hip flexor stretch (partial) | 1 |
| | | HIFLO03SL | Standing hip flexor stretch with back leg elevated | 3 |
| | HIIR L. C | HIIR001 CL | Side lying Isometric hip adduction and internal rotation | |
| | | HIIR002CB | Supine knee-to-knee adduction and internal rotation | |
| | | HIIR003CB | Supine hip adduction and internal rotation with a ball | " |
| Internal rotation of the left foot | | | | |
| | ANEV L. C | ANEVC001 CL | Seated ankle eversion with elastic resistance | |
| | HIER L. C | HIER001 CL | Side lying hip abductor/external rotator exercise | " |
| | | HIER002CB | Seated bilateral hip abductor/external rotator exercise | |
| | | HI ER003CL | Side lying hip abductor/external rotator contractions with a dumbbell | |
| | HIEX L. C | HIEX001CB | Supine pelvic tilt | |
| | | HIEX003CL | Supine pelvic tilt | 2,3 |
| | | HIEX004CL | Supine pelvic tilt with one leg extended at the knee | 3 |
| | | HIEX005CL | Kneeling hip extensor exercise (leg flexed at the knee) | 2 |
| | | HIEX006CL | Kneeling hip extensor exercise (leg extended) | 2,3 |
| | HIEX R. S | HIEX001SR | Standing hamstring stretch | |
| | | HIEX002SR | Supine hamstring stretch | 2,3 |
| | | HIEX003SR | Supine hamstring stretch | 1 |
| | | HIEX004SR | Supine hamstring stretch | 1 |
| | | HIEX007SR | Supine hamstring stretch | 1 |
| | | HIEX008SR | Supine hamstring stretch | 2,3 |
| | | HIEX011SR | Seated hamstring stretch | 2,3 |
| | | HIEX012SB | Seated bilateral hamstring stretch (legs apart) | |
| | | HIEX013SB | Seated bilateral hamstring stretch (legs together) | 3 |
| | | HIEX014SR | Standing hamstring stretch | 2,3 |
| | | HIEX015SR | Supine hamstring stretch | |
| | HIFL L. C | HIFL001CB | Squat | |
| | | TRFLO10CL | Abdominal crunch with unilateral hip flexion | 2,3 |
| | | TRFLO11 CL | Abdominal crunch with arms overhead and unilateral hip flexion | 2,3 |
| | | TRFLO12CB | Hip raises (lower abdominal contraction) | 3 |
| | HIFL R.S | HIFL001 SR | Standing hip flexor stretch | 2,3 |
| | | HIFLO02SR | Standing hip flexor stretch (partial) | 1 |
| | | HIFLO03SR | Standing tip flexor stretch with back leg elevated | 3 |

TABLE 3

| Body part | Action code | Description |
|---|---|---|
| Ankle (AN) | ANDL | Ankle dorsiflexion |
| | ANPF | Ankle plantar flexion |
| | ANIN | Ankle inversion |
| | ANEV | Ankle eversion |
| Elbow (EL) | ELFL | Elbow flexion |
| | ELEX | Elbow extension |
| | ELSU | Elbow supination (of forearm) |
| | ELPR | Elbow pronation (of forearm) |
| Hip (HI) | HIFL | Hip flexion |
| | HIEX | Hip extension |
| | HIAD | Hip adduction |
| | HIAB | Hip abduction |
| Knee (KN) | KNEX | Knee extension |
| | KNFL | Knee flexion |
| | KNIR | Knee internal rotation |
| | KNER | Knee external rotation |
| Neck Head (NH) | NHFL | Neck Head flexion |
| | NHEX | Neck Head extension |
| | NHFL | Neck Head lateral flexion |
| | NHIR | Neck Head ipsi-rotation |
| | NRCR | Neck Head contra-rotation |
| Scapula (SC) | SCEL | Scapula elevation |
| | SCDE | Scapula depression |
| | SCAB | Scapula abduction |
| | SCAD | Scapula adduction |
| | SCER | Scapula external rotation |
| | SCIR | Scapula internal rotation |
| | SCAN | Scapula anterior inclination |
| Shoulder (SH) | SHAB | Shoulder abduction |
| | SHAD | Shoulder adduction |
| | SHER | Shoulder external rotation |
| | SHFL | Shoulder flexion |
| | SHIR | Shoulder internal rotation |
| | SHEX | Shoulder extension |
| Trunk (TR) | TRFL | Trunk flexion |
| | TRLF | Trunk lateral flexion |
| | TRLE | Trunk lumbar extension |
| | TRTE | Trunk thoracic extension |
| | TRCE | Trunk cervical extension |
| | TRRO | Trunk rotation |
| Wrist (WR) | WRFL | Wrist flexion |
| | WREX | Wrist extension |
| | WRAB | Wrist abduction |
| | WRAD | Wrist adduction |

In a preferred embodiment of the present invention, the system generates a complete list of deviations for the client, in order of corrective priority. Priority is given to those deviations of body segments that are most perturbing to overall postural stability. Severity is also included in the decision making process, and only parameters exceeding critical values from correct vertical or horizontal alignment (of distance or angle) are considered deviations. These critical values were based on consultations with clinicians treating postural disorders and form a preliminary identification of severity. One of the advantages of the current system is that we will have access to large numbers of normative data from which severity rankings can be revised, as necessary. The first three ranked deviations in order of priority are automatically included in the design of the client's exercise and stretching program. The remaining deviations may be manually selected by the health-care professional based on his or her clinical experience and familiarity with the patient.

Table 4 shows the priority factors given to postural deviations.

TABLE 4

Deviations

| Code | Level | Name | Group | Factor | Priority | Actions | Formula |
|---|---|---|---|---|---|---|---|
| DIS001 | 1 | Translation of the | Neck Head | 50 | 50 | NHLF_R.C, NHLF_L.S | (((FA02X + FA03X)/2) >= FA06X + 10) AND (((FA02X + FA03X)/2) < FA06X + 20) AND (ABS(FA02X − FA04X) < 10) |
|  | 2 | Translation of the | Neck Head | 50 | 100 | NHLF_R.C, NHLF_L.S | (((FA02X + FA03X)/2) >= FA06X + 20) AND (ABS(FA02X − FA04X) < 10) |
| DIS002 | 1 | Translation of the | Neck Head | 50 | 50 | NHLF_L.C, NHLF_R.S | (((FA02X + FA03X)/2) <= FA06X − 10) AND (((FA02X + FA03X)/2) > FA06X − 20) AND (ABS(FA02X − FA04X) < 10) |
|  | 2 | Translation of the | Neck Head | 50 | 100 | NHLF_L.C, NHLF_R.S | (((FA02X + FA03X)/2) <= FA06X − 20) AND (ABS(FA02X − FA04X) < 10) |
| DIS003 | 1 | Protrusion of the h | Neck Head | 50 | 50 | TRCE.C,NHEX.S, NHFL.C | (SD01X >= SD04X + 25) AND (SD01X < SD04X + 50) |
|  | 2 | Protrusion of the h | Neck Head | 50 | 100 | TRCE.C,NHEX.S, NHFL.C | (SD01X >= SD04X + 50) |
| DIS004 | 1 | Posterior deviation | Neck Head | 50 | 50 | TRCE.S,NHEX.S, NHFL.S,NHFL.C | (SD01X <= SD04X − 25) AND (SD01X > SD04X − 50) |
|  | 2 | Posterior deviation | Neck Head | 50 | 100 | TRCE.S,NHEX.S, NHFL.S,NHFL.C | (SD01X <= SD04X − 50) |
| DIS005 | 1 | Flexion of the hea | Neck Head | 50 | 50 | TRCE.C,NHFL.C,NHEX.S | (SD02X >= SD03X + 20) AND (SD02X < SD03X + 35) |
|  | 2 | Flexion of the hea | Neck Head | 50 | 100 | TRCE.C,NHFL.CNHEX.S | (SD02X >= SD03X + 35) |
| DIS006 | 1 | Extension of the h | Neck Head | 50 | 50 | NHEX.C,NHFL.S,TRCE.C | (SD02X <= SD03X − 20) AND (SD02X > SD03X − 35) |
|  | 2 | Extension of the h | Neck Head | 50 | 100 | NHEX.C,NHFL.S,TRCE.C | (SD02X <= SD03X − 35) |
| DIS009 | 1 | Lateral flexion of t | Neck Head | 50 | 50 | NHLF_L.C,NHLF_R.S | (FA02X <= FA04X − 10) AND (FA02X > FA04X − 20) |
|  | 2 | Lateral flexion of t | Neck Head | 50 | 100 | NHLF_L.CNHLF_R.S | (FA02X <= FA04X − 20) |
| DIS010 | I | Lateral flexion of t | Neck Head | 50 | 50 | NHLF_R.CNHLF_L.S | (FA02X >= FA04X + 10) AND (FA02X < FA04X + 20) |
|  | 2 | Lateral flexion of t | Neck Head | 50 | 100 | NHLF_R.C,NHLF_L.S | (FA02X >= FA04X + 20) |
| DIS011 | 1 | Lateral translation | Trunk | 40 | 40 | TRLFj.C,TRLF_R.S,TRTE_R.S | (FA06 >= FAI0 + 20) AND (ABS(FA05Y − FA07Y) < 25) AND (FP03 <= FP08 − 20) AND (ABS(FP04Y − FP0SY) < 25) AND (FA06 < FA10 + 40) AND (FP03 > FP08 − 40) |
|  | 2 | Lateral translation | Trunk | 40 | 80 | TRLF_L.CTRLF_R.S, trte_R.S | (FA06 >= FA10 + 40) AND (ABS(FA05Y − FA07Y) < 25) AND (FP03 <= FP08 − 40) AND (ABS(FP04Y − FP05Y) < 25) |
| DIS012 | 1 | Lateral translation | Trunk | 40 | 40 | TRLF_R.CTRLF_L.S, TRTE_L.S | (FA06 <= FAI0 − 20) AND (ABS(FA05Y − FAVY) < 25) AND (FP03 >= FP08 + 20) AND < 25) AND (FA06 > FA10 − 40) AND (FP03 < FP08 + 40) |
|  | 2 | Lateral translation | Trunk | 40 | 80 | TRLF_R.CTRLF_L.S, TRT_E_L.S | (FA06 <= FA10 − 40) AND (ABS(FA05Y − FAVY) < 25) AND (FP03 >= FP08 + 40) AND (ABS(FP04Y − FP0SY) < 25) |
| DIS013 | 1 | Anterior deviation | Trunk + | 41 | 41 | TRLE.C,HIFL_L.S, HIFL_R.S, HIEX.S,SHAD.S,SCAD.C | (SD04X >= SD07X + 20) AND (SD04X > SD07X + 40) |
|  | 2 | Anterior deviation | Trunk + | 41 | 82 | TRLE.C,HIFL_L.S, HIFL_R.S,HIEX.S, SHAD.S,SCAD | (SD04X >= SD07X + 40) |
| DIS014 | 1 | Posterior deviation | Trunk + | 41 | 41 | TRLE.S,TRTE.S,TRFL.C, SCAD.S,HIFL_L.S, HIFL_R.S | (SD04X <= SD07X − 20) AND (SD04X > SD07X − 40) |
|  | 2 | Posterior deviation | Trunk + | 41 | 82 | TRLE.STRTE.S,TRFL.C, SCAD.S,HIFL_L.S, HIFL_R.S | (SD04X <= SD07X − 40) |

TABLE 4-continued

| | | | | | Deviations | | |
|---|---|---|---|---|---|---|---|
| Code | Level | Name | Group | Factor | Priority | Actions | Formula |
| DIS015 | 1 | Trunk flexion | Trunk | 40 | 40 | TRLE.CTRTE.C,HIFI.L.S, HIFL_R.S, NHEX.S,HIEX.S,SHAD.S | FALSE |
| DIS016 | 1 | Trunk extension | Trunk | 40 | 40 | TRLF_L.S,TRLF_R,S, TRTE.S,SCAD.S,SCAB.C, NHCX_L.S,NHEX_R.S | FALSE |
| DIS019 | 1 | Lateral flexion of t | Trunk + | 41 | 41 | TRLF_L.C,TRLF_R.S | (FA0SY <= FA07Y − 25) AND (FP04Y >= FP05Y + 25) AND (FA06X <= FAI0X − 25) AND (FP03X >= FP08X + 25) AND (FA0SY > FA07Y − S0) AND (FP04Y < FP0SY + 50) AND (FA06X > FA10X − S0) AND (FP03X < FP08X + S0) |
| | 2 | Lateral flexion of t | Trunk + | 41 | 82 | TRLF_L.C,TRLF_R.S | (FA05Y <= FA07Y − 50) AND (FP04Y >= FP0SY + 50) AND (FA06X <= FA10X − 50) AND (FP03X >= FP08X + 50) |
| DIS020 | 1 | Lateral flexion of t | Trunk + | 41 | 41 | TRLF_R.C,TRLF_L.S | (FA0SY >= FA07Y + 25) AND (FP04Y < FP05Y − 2S) AND (FA06X >= FA10X + 25) AND (FP03X <= FP08X − 25) AND (FA0SY < FA07Y + 50) AND (FP04Y > FP05Y − 50) AND (FA06X < FAI0X + 50) AND (FP03X > FP08X − 50) |
| | 2 | Lateral flexion of t | Trunk + | 41 | 82 | TRLF_R.C,TRLF_L.S | (FA05Y >= FA07Y + 50) AND (FP04Y <= FP0SY − 50) AND (FA06X >= FA10X + 50) AND (FP03X <= FP08X − 50) |
| DIS021 | 1 | Translation of the | Hip | 60 | 60 | HIAB_L.C.,HIAD_R.C, HIAB_R.S,HIAD_L.S | (FA10X >= FA17X + 20) AND (FA10X < FA17X + 40) |
| | 2 | Translation of the | Hip | 60 | 120 | HIAB_L.C,HIAD_R.C, HIAB_R.S,HIAD_L.S | (FAI0X >= FA17X + 40) |
| DIS022 | 1 | Translation of the | Hip | 60 | 60 | HIAB_R.C,HIAD_L.C, HIAB_L.S,HIAD_R.S | (FA17X >= FA10X + 20) AND (FA17X < FA10X + 40) |
| | 2 | Translation of the | Hip | 60 | 120 | HIAB_R.C,HIAD_L.C, HIAB_L.S,HIAD_R.S | (FAUX >= FA10X + 40) |
| DIS023 | 1 | Anterior translatio | Hip + | 61 | 61 | HIEX.C,HIFL_L.S, HIFL_R.S | (SD07X >= SD11X + 20) AND (SD07X < SD11X + 40) |
| | 2 | Anterior translatio | Hip + | 61 | 122 | HIEX.C,HIFL_L.S, HIFL_R.S | (SD07X >= SD11X + 40) |
| DIS024 | 1 | Posterior translatio | Hip + | 61 | 61 | HIFL_L.C,HIFLR.C, HIEX_L.S,HIEX_R.S | (SD11X >= SD07X + 20) AND (SD11X < SD07X + 40) |
| | 2 | Posterior translatio | Hip + | 61 | 122 | HIFl_L.C,HIFL_R.C, HIEX_L.S,HIEX_R.S | (SD11X − SD07X + 40) |
| DIS025 | 1 | Anterior pelvic tilt | Hip + | 61 | 61 | TRFL.C,HIEX.C,TRLE.S, HIFL_L.S,HIFL_R.S, HIEX_L.S,HIEX_R.S | (SD07X − SD09X >= 10) AND (SD07X − SD09X < 20) |
| | 2 | Anterior pelvic tilt | Hip + | 61 | 122 | TRLE.C,HIEX.C,TRLE.S, HIFL_L.S,HIFL_R.S, HIEX_L.5,HIEX_R.S | (SD07X − SD09X >= 20) |
| DN026 | 1 | Posterior pelvic tilt | Hip + | 61 | 61 | TRLE.C,HIFL_L.C, HIFL_R.C,TRFL.S, HIEX_L.S,HIEX_R.S | (SD09X − SD07X >= 10) AND (SD09X − SD07X < 20) |
| | 2 | Posterior pelvic tilt | Hip + | 61 | 122 | TRLE.C,HIFL_L.C, HIFL_R.C,TRFL.S, HIEX_L.S,HIEX_R.S | (SD09X − SD07X >= 20) |
| DIS029 | 1 | Lateral elevation o | Hip | 60 | 60 | TRLE.CTRTE.C,TRFL.S, TRLF_R.C,TRLF_L.S | (FA11 − FA09 >= 10) AND (FAII − FA09 < 20) |
| | 2 | Lateral elevation o | Hip | 60 | 120 | TRLE.CTRTE.C, TRFL.STRLF_R.C, TRLF_L.S | (FA11 − FA09 >= 20) |
| DIS030 | 1 | Lateral elevation o | Hip | 60 | 60 | TRLE.S,TRTE.S, TRFL.CTRLF_L.C,TRLFR.S | (FA09 − FA1I >= 10) AND (FA09 − FAII < 20) |
| | 2 | Lateral elevation o | Hip | 60 | 120 | TRLE.S,TRTE.S, TRFL.CTRLF_L.C, TRLF_R.S | (FA09 − FA11 >= 20) |
| DIS031 | 1 | Plantar flexion of t | Unknown | 0 | 0 | AND F_R.C,ANPF_R,S | (SD10X − SD11X >= 20) AND (SD10X − SDIIX < 40) |
| | 2 | Plantar flexion of t | Unknown | 0 | 0 | AND F_R.C,ANPF_R.S | (SD10X − SD11X >= 40) |
| DIS032 | 1 | Dorsiflexion of the | Unknown | 0 | 0 | ANPF_R.C, AND F_R.S | (SD11X − SD10X >= 20) AND (SD1IX − SD10X < 40) |
| | 2 | Dorsiflexion of the | Unknown | 0 | 0 | ANPF_R.C, AND F_R.S | (SD11X − SD10X >= 40) |

TABLE 4-continued

Deviations

| Code | Level | Name | Group | Factor | Priority | Actions | Formula |
|---|---|---|---|---|---|---|---|
| DIS033 | 1 | Internal rotation of | Ankle + | 11 | 11 | HIFL_R.C,HIEX_R.C, HIER_R.C,HIFL.L.S, HIEX_L.S,ANEV_R.C | (FA19X − FA16X >= 10) AND (FA19X − FA16X < 20) |
|  | 2 | Internal rotation of | Ankle + | 11 | 22 | HIFL_R.C,HIEX_R.C, HIER_R.C,HIFL.L.5, HIEX_L.S,ANEV_R.C | (FA19X − FA16X >= 20) |
| DIS034 | 1 | External rotation o | Ankle + | 11 | 11 | HIIR_R.C,HIFL_R.S, HIEX_R.S,HIER_R.S, ANIN_R.C | (FA16X − FA19X >= 10) AND (FA16X − FA19X < 20) |
|  | 2 | External rotation o | Ankle + | 11 | 22 | HIIR_R.C,HIFL_R.S, HIEX_R.S,HIER_R.S, ANIN_R | (FA16X − FA19X >= 20) |
| DIS037 | 1 | Genu valgum right | Knee | 20 | 20 | HIAD_R.C,HIAB_R.S | (FA14X − FA09X >= 10) AND (FA14X − FA16X >= 10) AND ((FA14X − FA09X < 20) OR (FA14X − FA16X < 20)) |
|  | 2 | Genu valgum right | Knee | 20 | 40 | HIAD_R.C,HIAB_R.S | FA14X − FA09X >= 20) AND (FA14X − FA16X >= 20) |
| DIS038 | 1 | Genu valgum left | Knee | 20 | 20 | HIAD_L.C,HIAB_L.S | (FA11X − FA15X >= 10) AND (FA18X − FA15X >= 10) AND ((FA11X − FA15X < 20) OR (FA18X − FA15X < 20)) |
|  | 2 | Genu valgum left | Knee | 20 | 40 | HIAD_L.C,HIAB_L.S | (FA11X − FA15X >= 20) AND (FA18X − FA15X >= 20) |
| DIS039 | 1 | Genu varum right | Knee | 20 | 20 | HIAB_R.C,HIAD_R.S | (FA09X − FA14X >= 10) AND (FA16X − FA14X >= 10) AND ((FA09X − FA14X < 20) OR (FA16X − FA14X < 20)) |
|  | 2 | Genu varum right | Knee | 20 | 40 | HIAB_R.C,HIAD_R.S | (FA09X − FA14X >= 20) AND (FA16X − FA14X > 20) |
| DIS040 | 1 | Genu varum left | Knee | 20 | 20 | HIAB_L.C,HIAD_L.S | (FA15X − FA11X >= 10) AND (FA15X − FA18X >= 10) AND ((FA15X − FA11X < 20) OR (FA15X − FA18X < 20)) |
|  | 2 | Genu varum left | Knee | 20 | 40 | HIAB_L.C,HIAD_L.S | (FA15X − FA11X >= 20) AND (FA15X − FA18X >= 20) |
| DIS041 | 1 | Anterior deviation | Shoulder | 30 | 30 | SCAD.C,SHFL.S,SHIR.S | (SD04X − SD01X >= 10) AND (SD04X − SD07X >= 10) AND ((SD04X − SD01X < 20)OR (SD04X − SD07X < 20)) |
|  | 2 | Anterior deviation | Shoulder | 30 | 60 | SCAD.C,SHFL.S,SHIR.S | (SD04X − SD01X >= 20) AND (SD04X − SD07X >= 20) |
| DIS042 | 1 | Posterior deviation | Shoulder | 30 | 30 | SCAD.S,SHFL.C,SHIR.C, SCAB.C | (SD01X − SDD4X >= 10) AND (SD07X − SD04X >= 10) AND ((SD01X − SD04X < 20)OR (SD07X − SD04X < 20)) |
|  | 2 | Posterior deviation | Shoulder | 30 | 60 | SCAD.S,SHFL.C,SHIR.C, SCAB.C | (SD01X − SD04X >= 20) AND (SD07X − SD04X >= 20) |
| DIS043 | 1 | External rotation o | Ankle + | 11 | 11 | HIIR_L.C,HIFL_L.S, HIEX_L.S,HIER_L.S, ANIN_L.C | (FA20X − FA18X >= 10) AND (FA20X − FA18X < 20) |
|  | 2 | External rotation o | Ankle + | 11 | 22 | HIIR_L.C,HIFL_L.S, HIEX_L.S,HIER_L.S, ANIN_L | (FA20X − FA18X >= 20) |
| DIS044 | 1 | Internal rotation of | Ankle + | 11 | 11 | HIFL_L.C,HIEX_L.C, HIER_L.C,HIFLR.C, HIEXR.S,ANEV_L.C | (FA18X − FA20X >= 10) AND (FA18X − FA20X < 20) |
|  | 2 | Internal rotation of | Ankle + | 11 | 22 | HIFL L_C,HIEX_L.C, HIER_L.C,HIFL_R.S, HIEX_R.S,ANEV_L | (FA18X − FA20X >= 20) |

As stated previously, each deviation is linked to corrective actions and these actions, in turn, are linked to appropriate exercises and stretching routines to treat the deviation. The corrective actions are linked to their deviations by a code that specifies the type of action and exercise required to correct the identified deviation. Every exercise is associated with a level of difficulty from one to three. When beginning a biomechanical assessment, the health-care professional indicates his client's activity level from one to three (level 1=inactive, level 2=moderately active, level 3=highly active and *=all levels of activity). Only those exercises matching the client's activity level are selected to treat any particular deviation.

A client's exercise schedule is divided into three sessions: the first is of two weeks in duration and the last two are of four weeks duration. When an action group contains numerous exercises, the system always selects only the first three exercises and inserts one into each session. When there is only one exercise applicable, it is included in all three sessions. If there are two exercises applicable, the first is slotted into session 1, and the second one into sessions 2 and 3. There is a maximum of twelve exercises applicable per session. When the system calculates more than twelve exercises applicable per session, the user is requested to delete a deviation. This self-regulating process ensures that the entire 10-week exercise program does not include more than thirty-six exercises, and that not more than 12 are prescribed in one week in order to respect a maximum time budget allowed.

In one other embodiment of the present invention, an artificial neural network is trained to select exercises based on biomechanical segments points coordinates without passing through all previously shown calculations.

The patient's personal information, images, biomechanical assessment, postural deviations, corrective actions and associated exercises and stretches are presented in the Biomechanical Assessment Report that is printed by the practitioner. A page from a sample Biomechanical Assessment Report is presented in FIG. 13. Presented are personal information on the patient(l), lateral view image of the patient with markers (2), and biomechanical parameters. Presented in FIG. 14 is a page from the same sample Biomechanical Assessment Report that includes specification of the patient's postural deviations and the associated exercises and stretching. Presented in FIG. 15 is a page from the Postural Analysis Report that displays the exercise schedule generated in the Biomechanical Assessment process. This figure details the personalized exercise routines for the 10-week treatment period. Finally, presented in FIG. 16 is another page from the Biomechanical Assessment Report illustrating and describing a few of the exercises of the exercise schedule. All of the above information is generated automatically (and modifiable manually) by the system.

In a preferred embodiment of the present invention, after the patient has completed the exercise routines, he or she, can return for a follow-up evaluation. Feedback is given by the health-care pratitionner and new images of the patient are taken in order to reevaluate deviations and priorities. A comparative Biomechanical Assessment Report is generated comparing two assessments. The goal is to assess the effects of treatment and modify the exercise regime, if necessary. A quantified analysis of improvement is therefore provided and both the patient and health-care practitioner can visualize progress towards ideal postural alignment. In another embodiment of the present invention, feedback is provided directly by the patient through the web site, such information being used as a complement in the postural evaluation and in further exercise selection.

Importantly, all biomechanical data linked to personal information parameters such as height, weight, and age are stored centrally. In one embodiment of the invention, correlation is executed between the personal information parameters, the exercises selected in the Biomechanical Assessment and between the improvement of the patient's condition. This correlation allows the determination of the exercises which are more efficient for the different elements associated with the patient such as the deviation severity, the age, the gender or the activity level. Parameters used in deviation-exercises correlation are adjusted based on the effectiveness of the exercise program to correct deviations and the exercise program is repeatedly varied until the effectiveness of the exercises is optimized. An important advantage of having calculations performed centrally rather than on locally arranged software, is that improvements and modifications to the system can be made instantaneously across users without delays cause by the more standard transmission of software updates. This is a highly distinguishing aspect of our Biomechanical Assessment system. An additional distinguishing feature is that biomechanical assessments can be peformed at remote locations, as the digital image acquisition can be performed virtually anywhere. Web-based technology is ideally placed to bring cutting-edge health care to potentially disadvantage geographical locations.

While the invention has been described in connection with specific embodiments thereof, it will be understood that it is capable of further modification and this application is intended to cover any variations, uses, or adaptations of the invention following, in general, the principles of the invention and including such departures from the present disclosure as come within known or customary practice within the art to which the invention pertains and as may be applied to the essential features here in before set forth, and as follows in the scope of the appended claims.

What is claimed is:

1. A method of acquiring biomechanical position data for use in postural analysis, the method comprising the steps of:
    a) selecting a plurality of marker positions referenced with respect to an anatomy of a patient by one of:
        skin surface features having minimal variability from one patient to the next; and
        skeletal features palpable from a skin surface of the patient;
    b) attaching a scanable marker on the patient at each of the marker positions, the step of attaching including palpating the patient to define at least some of the marker positions;
    c) instructing the patient to stand relaxed and in normal posture; and
    d) scanning the markers attached to the patient to obtain position data for each of the marker positions.

2. The method as claimed in claim 1, wherein the patient is scanned from a front, side and rear viewpoint.

3. The method as claimed in claim 2, wherein the step of scanning comprises photographing the patient against a backdrop, the markers comprising contrasting visual markers, the backdrop including a plurality of scale and orientation reference marker points.

4. The method as claimed in claim 3, wherein the markers comprise an adhesive layer for sticking to the patient.

5. The method as claimed in claim 4, wherein the step of photographing comprises using a digital camera with a flash to obtain digital images, the markers comprising retroreflective markers.

6. The method as claimed in claim 5, wherein some of the markers are scanned from more than one of the viewpoints and comprise retroreflective spheres.

7. The method as claimed in claim 3, wherein the step of instructing the patient to stand relaxed and in normal posture comprises requesting the patient to walk in place prior to standing still.

8. The method as claimed in claim 5, wherein the step of scanning comprises automatically recognizing the markers and the reference marker points in the digital images using a computer.

9. The method as claimed in claim 8, wherein the computer comprises a user interface and, when the computer recognizes too many or too few of the markers, input is accepted via the user interface to remove or add, with reference to the digital images, the position coordinates of the markers which the computer incorrectly recognized or failed to recognize.

10. A method for calculating postural deviation values in a patient comprising the steps of:

a) obtaining position data identifying a position in space of body segments of the patient while standing relaxed and in normal posture, the body segments comprising head-shoulders, shoulders-pelvis, pelvis-hips, hips-knees and knees-ankles;

b) obtaining weight data of the patient;

c) calculating vertical and horizontal plumb lines using the position data;

d) calculating for at least some of the body segments an angle of deviation value and distance of deviation value with respect to plumb lines position value using the position data.

11. The method as claimed in claim 10, wherein the angle and distance of deviation values are referenced with respect to average or normal values.

12. The method as claimed in claim 10, further comprising a step of calculating an effective weight or stress of at least one of the body segments using an estimated weight of the at least one body segment and the deviation values.

13. The method as claimed in claim 10, wherein the deviation values are calculated for all of the body segments.

14. A method of selecting exercises for improving tonicity and correcting posture in a patient, the method comprising the steps of:

a) obtaining biomechanical position data of the patient while standing relaxed and in normal posture, the position data being indicative of postural problems requiring correction;

b) ranking the postural problems by severity and priority;

c) correlating the position data with exercises for strengthing or stretching specific muscles or muscle groups to obtain ranking data for the exercises;

d) compiling an exercise program for the patient based on the ranking data.

15. The method as claimed in claim 14, wherein the step of compiling comprises manually selecting exercises from a ranked list of exercises.

16. The method as claimed in claim 15, wherein the exercises are grouped in sets of exercises each attempting to correct a specific postural deviation, the step of correlating comprising correlating the position data with the sets of exercises, and the exercise program comprising a series of the sets of exercises.

17. The method as claimed in claim 14, wherein the exercises are grouped in sets of exercises each attempting to correct a specific postural deviation, the step of correlating comprising correlating the position data with the sets of exercises, and the exercise program comprising a series of the sets of exercises.

18. The method as claimed in claim 14, wherein the position data identifies a position in space of body segments of the patient, the body segments comprising head-shoulders, shoulders-pelvis, pelvis-hips, hips-knees and knees-ankles, and the step of correlating comprises:

a) calculating a center of mass plumb line position value using the position data and weight data;

b) calculating for at least some of the body segments an angle of deviation value and distance of deviation value with respect to the plumb line position value using the position data;

c) comparing the deviation values to normal values for the at least some of the body segments to obtain deviation priority values;

d) ranking the deviation priority values according to an order of severity or importance; and e) determining the ranking data based on an association of the exercises with body segment deviations in accordance with the order of severity or importance.

19. The method as claimed in claim 18, wherein the step of ranking the deviation priority values according to an order of severity or importance comprises manually selecting deviations to be corrected by the exercise program, the order of severity or importance reflecting those deviations manually selected.

20. The method as claimed in claim 19, wherein the exercises are grouped in sets of exercises each attempting to correct a specific postural deviation, and the exercise program comprising a series of the sets of exercises.

21. The method as claimed in claim 20, wherein the exercise program is limited to a maximum number of exercises, the step of manually selecting deviations is automatically restricted when a maximum number of exercises corresponding to the selected deviations exceeds the maximum number for the exercise program.

22. The method as claimed in claim 14, wherein the step of compiling comprises repeating ones of the exercises corresponding to most severe postural problems regularly throughout the exercise program and including ones of the exercises corresponding to less severe postural problems for only part of the program.

23. The method as claimed in claim 22, wherein the step of compiling comprises including ones of the exercises corresponding to moderately severe postural problems more intensively for only part of the exercise program.

24. The method as claimed in claim 18, wherein the step of compiling comprises repeating ones of the exercises corresponding to most severe postural problems regularly throughout the exercise program and including ones of the exercises corresponding to less severe postural problems for only part of the program.

25. The method as claimed in claim 24, wherein the step of compiling comprises including ones of the exercises corresponding to moderately severe postural problems more intensively for only part of the exercise program.

26. The method as claimed in claim 14, further comprising steps of:

a) obtaining, after completing of the exercise program, new biomechanical position data of the patient while standing relaxed and in normal posture;

b) evaluating an effectiveness of the exercises in the exercise program for correcting the postural problems; and c) adjusting parameters used in the step of correlating for future patients based on the effectiveness evaluated in the previous step.

27. The method as claimed in claim 26, wherein the exercise program is repeatedly varied until the effectiveness of the exercises is optimized.

28. The method as claimed in claim 27, wherein the steps of correlating, evaluating and adjusting are carried out using a centralized shared database of the parameters used in the step of correlating for a large number of patients.

29. The method as claimed in claim 26, wherein the parameters include at least one of age, gender and an activity level of the patient.

30. A method of providing posture health care using a distributed system, the method comprising the steps of:

a) obtaining personal data of a patient, the personal data including weight, height, gender and activity data of the patient, and obtaining posture anatomical reference position data of the patient at a biomechanical measurement station;

b) processing the personal and position data using data stored in a remote central database to obtain preliminary postural deviation assessment data;

c) providing the preliminary postural deviation assessment data to one of a health-care practitioner and the patient;

d) obtaining corrected postural deviation assessment data from one of the health-care practitioner and the patient; and e) modifying the data stored in the central database using the corrected data.

31. The method as claimed in claim 30, wherein the preliminary postural deviation assessment data comprises a ranked list of deviations and a preliminary selection of the deviations to be included in a therapeutic exercise program, and the corrected data comprises a corrected selection of the deviations to be included in a therapeutic exercise program.

32. The method as claimed in claim 30, wherein:

the preliminary postural deviation assessment data comprises a set of therapeutic exercises of an exercise program;

the corrected data comprises new posture anatomical reference position data of the patient obtained after completion of the exercise program; and step (e) comprises processing the new reference position data to determine an effectiveness of the therapeutic exercises in correcting postural deviations and modifying accordingly the data stored in the central database.

33. The method as claimed in claim 30, wherein:

step (a) comprises validating completeness of the reference position data at the biomechanical measurement station and transmiting the personal and position data to a central server;

step (b) is a carried out at the central server;

step (c) comprises transmitting the preliminary postural deviation assessment data from the central server to one of the health-care practitioner and the patient;

step (d) comprises transmitting the corrected data to the central server; and step (e) is carried out by the central server.

34. The method as claimed in claim 33, wherein the biomechanical measurement station includes a health-care practitioner client station in communication with the central server.

35. The method as claimed in claim 34, wherein the client station uses a web browser interface to communicate with the central server, the central server providing a secure connection to a biomechanical assessment report web document for the patient.

* * * * *